United States Patent
Weissberg et al.

(10) Patent No.: US 9,656,055 B2
(45) Date of Patent: May 23, 2017

(54) IN VIVO TREATMENT OF SKIN LESIONS BY ELECTRICAL NANOPULSES

(71) Applicant: Pulse Biosciences, Inc., Burlingame, CA (US)

(72) Inventors: Jack Robert Weissberg, Culver City, CA (US); Gary Steven Lazar, Encino, CA (US); Dong Yin, Valencia, CA (US)

(73) Assignee: PULSE BIOSCIENCES, INC., Burlingame, CA (US)

( * ) Notice: Subject to any disclaimer, the term of this patent is extended or adjusted under 35 U.S.C. 154(b) by 5 days.

(21) Appl. No.: 13/631,618

(22) Filed: Sep. 28, 2012

(65) Prior Publication Data

US 2013/0041443 A1    Feb. 14, 2013

Related U.S. Application Data

(63) Continuation-in-part of application No. 13/565,630, filed on Aug. 2, 2012, now abandoned.

(60) Provisional application No. 61/514,733, filed on Aug. 3, 2011.

(51) Int. Cl.
| | |
|---|---|
| A61N 1/00 | (2006.01) |
| A61N 1/05 | (2006.01) |
| A61N 1/32 | (2006.01) |
| C12N 13/00 | (2006.01) |
| A61B 18/12 | (2006.01) |
| H03K 3/53 | (2006.01) |
| A61B 18/00 | (2006.01) |
| A61B 18/14 | (2006.01) |

(52) U.S. Cl.
CPC .......... *A61N 1/0502* (2013.01); *A61N 1/328* (2013.01); *C12N 13/00* (2013.01); *A61B 18/1206* (2013.01); *A61B 2018/00452* (2013.01); *A61B 2018/143* (2013.01); *H03K 3/53* (2013.01)

(58) Field of Classification Search
CPC .. A61N 1/0502; A61N 1/328; A61B 18/1206; A61B 2018/143; A61B 2018/00452; C12N 13/00; H03K 3/53
USPC ........................................................ 607/115
See application file for complete search history.

(56) References Cited

U.S. PATENT DOCUMENTS

| | | | |
|---|---|---|---|
| 6,326,177 B1 | 12/2001 | Schoenbach et al. | |
| 6,426,666 B1 | 7/2002 | Li et al. | |
| 6,831,377 B2 | 12/2004 | Yampolsky et al. | |
| 7,483,738 B2 * | 1/2009 | Tamarkin et al. | ................ 607/3 |

(Continued)

FOREIGN PATENT DOCUMENTS

WO    2010/011408 A1    1/2010

OTHER PUBLICATIONS

Beebe S.J. 2003. Diverse Effects of Nanosecond Pulsed Electric Fields on Cells and Tissues, DNA and Cell Biology, vol. 22, No. 12, 2003, pp. 785-796.

(Continued)

*Primary Examiner* — Mallika D Fairchild
(74) *Attorney, Agent, or Firm* — Kilpatrick Townsend & Stockton LLP

(57) ABSTRACT

This disclosure relates to an in vivo treatment of a skin lesion of a mammal comprising application of electrical energy to the skin lesion in a form of electrical pulses. At least one electrical pulse is applied. The pulse duration may be at least 0.01 nanoseconds at the full-width-at-half-maximum. This treatment may at least prevent growth of the lesion.

34 Claims, 6 Drawing Sheets

(56) References Cited

U.S. PATENT DOCUMENTS

| | | | |
|---|---|---|---|
| 7,767,433 | B2 | 8/2010 | Kuthi et al. |
| 7,901,929 | B2 | 3/2011 | Kuthi et al. |
| 7,901,930 | B2 | 3/2011 | Kuthi et al. |
| 8,115,343 | B2 | 2/2012 | Sanders et al. |
| 8,120,207 | B2 | 2/2012 | Sanders et al. |
| 2005/0218423 | A1 | 10/2005 | Shimizu et al. |
| 2006/0062074 | A1 | 3/2006 | Gundersen et al. |
| 2007/0031959 | A1 | 2/2007 | Kuthi et al. |
| 2008/0231337 | A1 | 9/2008 | Krishnaswamy et al. |
| 2009/0299417 | A1* | 12/2009 | Schoenbach ............ A61N 1/327 607/2 |
| 2010/0038971 | A1 | 2/2010 | Sanders et al. |
| 2010/0130972 | A1* | 5/2010 | Yambor et al. ................. 606/34 |
| 2010/0222734 | A1* | 9/2010 | Jayes et al. ...................... 604/20 |
| 2010/0274327 | A1* | 10/2010 | Carroll ................. A61N 1/0456 607/72 |
| 2012/0109263 | A1* | 5/2012 | Kolb et al. ...................... 607/72 |

OTHER PUBLICATIONS

Nucitelli R. 2006. Nanosecond pulsed electric fields cause melanomas to self-destruct, Biochemical and Biophysical Research Communications, vol. 343, pp. 351-360.
Ren W. 2011. An apoptosis targeted stimulus with nanosecond pulsed electric fields (nsPEFs) in E4 squamous cell carcinoma, Apoptosis, vol. 16, pp. 382-393.
Sylvester P.W. 2005. Effects of ultra-wideband electromagnetic pulses on pre-neoplastic mammary epithelial cell proliferation,Cell Prolif., vol. 38, pp. 153-163.
Yin D. 2012. Cutaneous Papilloma and Squamous Cell Carcinoma Therapy Utilizing Nanosecond Pulsed Electric Fields (nsPEF), PLoS One vol. 7, No. 8, pp. e43891-e43891.
Barth RF. 1998. Rat brain tumor models in experimental neuro-oncology: the 9L, C6, T9, F98, RG2 (D47), RT-2 and CNS-1 gliomas. J Neurooncol. 36(1): pp. 91-102.
Bier M. et al. 1999. Kinetics of Sealing for Transient Electropores in Isolated Mammalian Skeletal Muscle Cells, Bioelectromagnetics, v20, pp. 194-201.
Borner M. et al. 1994. The detergent Triton X-100 induces a death pattern in human carcinoma cell lines that resembles cytotoxic lymphocyte-induced apoptosis. FEBS Lett. 353: pp. 129-132.
Cole MJ et al. 2001. Time-domain whole-field fluorescence lifetime imaging with optical sectioning; Journal of Microscopy, vol. 203, Pt. 3, Sep. 2001, pp. 246-257.
Cossarizza A et al. 2001. Chapter 21 Analysis of Mitochondria during Cell Death. In Methods in Cell Biology, vol. 63, pp. 467-486.
Craft CM et al. 1998. PhLPs and PhLOPs in the phosducin family of G beta gamma binding proteins. American Chemical Society, Biochemistry 37: pp. 15758-15772.
Cubeddu R et al. 2002. Time-resolved fluorescence imaging in biology and medicine; Topical Review; Institute of Physics Publishing, J. Phys.D; Appl.Phys, 35: pp. R61-R76.
DeAngelis LM 2001. Brain Tumors. New England Journal of Medicine, v. 344: pp. 114-123.
DeBruin KA et al. 1999. Modeling electroporation in a single cell. I. Effects of field strength and rest potential. Biophysical Journal, vol. 77, Sep. 1999: pp. 1213-1224.
Frank K et al. 1998. High power pseudospark and BLT switches. IEEE Trans. Plasma Science 16 (2): pp. 317-323.
Freeman SA et al. 1994. Theory of electroporation of planar bilayer membranes: predictions of the aqueous area, change in capacitance, and pore-pore separation. Biophysical Journal, vol. 67, Jul. 1994: pp. 42-56.
Garon et al. 2007. In Vitro and In Vivo Evaluation and a Case Report of Intense Nanosecond Pulsed Electric Field as a Local Therapy for Human Malignancies. Int. J. Cancer, vol. 121, pp. 675-682.
Gilbert RA et al. 1997. Novel electrode designs for electrochemotherapy. Biochimica et Biophys. Acta vol. 1334, pp. 9-14.
Gotoh T et al. 2002. Nitric Oxide-induced Apoptosis in RAW 264.7 Macrophages I s Mediated by Endoplasmic Reticulum Stress Pathway Involving ATF6 and CHOP. J. Biol. Chem. vol. 277, No. 14, Apr. 2002: pp. 12343-12350.
Grekhov IV et al. 1983. Formation of Nanosecond High-Voltage Drop Across Semiconductor Diodes with Voltage Recovery by a Drift Mechanism. Sov. Tech Phys. Lett., vol. 9, No. 4: pp. 188-189.
Grekhov, IV et al. 2000 Physical Basis for High-Power Semiconductor Nanosecond Opening Switches. IEEE Transactions on Plasma Science, vol. 28: pp. 1540-1544.
Grekhov IV et al. 2005. Nanosecond Semiconductor Diodes for Pulsed Power Switching. Physics-Uspekhi, vol. 48, No. 7: pp. 703-712.
Gundersen, M. et al. 2004. Nanosecond Pulse Generator Using a Fast Recovery Diode. IEEE 26.sup.th Power Modulator Conference, pp. 603-606.
Hemker RG et al. 1999. Development of a parallel code for modeling plasma based accelerators. IEEE Particle Accelerator Conference 5: pp. 3672-3674.
Hennings, H. et al. 1985. Induction of papillomas with a high probability of conversion to malignancy. Carcinogenesis vol. 6, pp. 1607-1610.
Hennings, H. et al. 1986. Malignant conversion and metastasis of mouse skin tumors: a comparison of SENCAR and CD-1 mice. Environmental health perspectives, vol. 68, pp. 69-74.
Hewlett Packard. 1984. Application Note 918, Pulse and Waveform Generation with Step Recovery Diodes. Oct. 1984. 22 pages.
International Search Report for PCT Application Serial No. PCT/US09/45073, mailed Dec. 18, 2009, entitled "Nanosecond Pulse Generator," Sanders et al., inventors, filed May 22, 2009, published Jan. 28, 2010, as WO 2010/011408 A1.
Joshi RP et al. 2000. Electroporation dynamics in biological cells subjected to ultrafast electrical pulses: a numerical simulation study, Physical Review E, vol. 62, Jul. 2000: pp. 1025-1033.
Kirkman GF et al. 1986. Low pressure, light initiated, glow discharge switch for high power applications. Appl. Phys. Lett., vol. 49, Sep. 1986: pp. 494-495.
Kotnik T et al. 2000. Theoretical evaluation of the distributed power dissipation in biological cells exposed to electric fields, Bioelectromagnetics, vol. 21: pp. 385-394.
Kotov, YuA et al. A 1993. Novel Nanosecond Semiconductor Opening Switch for Megavolt Repetitive Pulsed Power Technology: Experiment and Applications. In Proceedings of the 9th Int. IEEE Pulsed Power Conference, Albuquerque, NM, 1993, pp. 134-139.
Li A et al. 2002. Retinoic acid upregulates cone arrestin expression in retinoblastoma cells through a Cis element in the distal promoter region. Invest Ophthalmol Vis Sci., vol. 43, No. 5, May 2002: pp. 1375-1383.
Li A et al. 2003. Gene expression networks underlying retinoic acid-induced differentiation of human retinoblastoma Cells Invest Ophthalmology & Vision Science, vol. 44, No. 3, Mar. 2003: pp. 996-1007.
Lyubutin SK et al. 1997. Repetitive Nanosecond All-Solid-State Pulsers Based on SOS Diodes. In IEEE 11th International Pulsed Power Conference, Baltimore, MD: pp. 992-998.
Marcu L et al. 1999. Photobleaching of arterial fluorescent compounds: Characterization of elastin, collagen, and cholesterol time-resolved spectra during prolonged ultraviolet irradiation, Photochem. Photobiol., vol. 69, No. 6: pp. 713-721.
Marszalek P et al. 1990. Schwan equation and transmembrane potential induced by alternating electric field, Biophysical Journal, vol. 58, Oct. 1990: pp. 1053-1058.
Maytin EV et al. 2001. Stress-Inducible Transcription Factor CHOP/gadd153 Induces Apoptosis in Mammalian Cells via p38 Kinase-Dependent and -Independent Mechanisms. Exp. Cell Res., vol. 267: pp. 193-204.
Moll, JL et al. 1969. Physical Modeling of the Step Recovery Diode for Pulse and Harmonic Generation Circuits. In Proceedings of the IEEE, vol. 57, No. 7, Jul. 1969: pp. 1250-1259.
Pogue BW et al. 2001. In vivo NADH Fluorescence Monitoring as an Assay for Cellular Damage in Photodynamic Therapy; Photochemistry and Photobiology, vol. 74, No. 6, Oct. 2001: pp. 817-824.

(56) References Cited

OTHER PUBLICATIONS

Polevaya Y et al. 1999. Time domain dielectric spectroscopy study of human cells. II. Normal and malignant white blood cells. Biochim. Biophys. Acta., vol. 1419: pp. 257-271.

Rukin, SN. 1999. High-Power Nanosecond Pulse Generators Based on Semiconductor Opening Switches (Review). Instruments and Experimental Techniques, vol. 42, No. 4: pp. 439-467.

Sanders J. et al. 2008. Broadband Power Measurement of High-Voltage, Nanosecond Electric Pulses for Biomedical Applications. IEEE International Power Modulator Conference, Las Vegas, NV, 2008, pp. 350-353.

Schoenbach KH et al. 1997. The Effect of Pulsed Electric Fields on Biological Cells: Experiments and Applications, IEEE Transactions on Plasma Science, vol. 25, Apr. 1997: pp. 284-292.

Slaga, T.J. 1986. SENCAR mouse skin tumorigenesis model versus other strains and stocks of mice. Environmental health perspectives, vol. 68, pp. 27-32.

Tang, et al. 2007. Diode Opening Switch Based Nanosecond High Voltage Pulse Generators for Biological and Medical Applications. IEEE Transactions on Dielectrics and Electrical Insulation, vol. 14, No. 4, pp. 878-883.

Wakita M et al. 1995. Some Characteristics of the Fluorescence Lifetime of Reduced Pyridine Nucleotides in Isolated Mitochondria, Isolated Hepatocytes, and Perfused Rat Liver In Situ. J. Biochem., vol. 118: pp. 1151-1160.

Wang F et al. 2005. Solid-State High Voltage Nanosecond Pulse Generator. IEEE Pulsed Power Conference, pp. 1199-1202.

Watanabe K et al. 2002. Feasibility and limitations of the rat glioma model by C6 gliomas implanted—at the subcutaneous region. Neurol. Res., vol. 24, No. 5, Jul. 2002: pp. 485-490.

Weaver JC et al. 1996. Theory of Electroporation: A Review. Bioelectrochemistry and Bioenergetics, vol. 41: pp. 135-160.

Webb SED et al. 2002. A wide-field time-domain fluorescence lifetime imaging microscope with optical sectioning. Review of Scientific Instruments, vol. 73, No. 4, Apr. 2002: pp. 1898-1907.

Weiss A et al. 1984. The Role of T3 surface molecules in the activation of human t cells: A two-stimulus requirement for IL 2 production reflects events occurring at a pre-translational level. The Journal Immunology, vol. 133, No. 1, Jul. 1984: pp. 123-128.

Zhu X et al. 2000. The carboxyl terminal domain of phosducin functions as a transcriptional activator. Biochemical and Biophysical Research Communications, vol. 270: pp. 504-509.

Zhu X et al. 2002. Mouse Cone Arrestin Gene Characterization: Promoter Targets Expression to Cone Photoreceptors. FEBS Letters, vol. 425: pp. 116-122.

\* cited by examiner

Example 36
Skin Lesion
Before Treatment

Example 3
Skin Lesion
Before Treatment

IN VIVO TREATMENT OF SKIN LESIONS BY ELECTRICAL NANOPULSES

CROSS-REFERENCE TO RELATED APPLICATIONS

This application is a continuation-in-part of prior application Ser. No. 13/565,630, filed Aug. 2, 2012, entitled "In Vivo Treatment of Skin Lesions by Electrical Nanopulses," which is based upon and claims priority to U.S. Provisional Application No. 61/514,733, filed Aug. 3, 2011. The entire content of both applications is incorporated herein by reference.

BACKGROUND

Technical Field

This disclosure relates to in vivo treatment of skin lesions of mammals and to application of electrical pulses with a duration of 1,000 nanoseconds or less.

Description of Related Art

Ultra-short, high-field strength electric pulses may be used in the electroperturbation of biological cells. For example, these electric pulses may be used in treatment of human cells and tissue including tumor cells, such as basal cell carcinoma, squamous cell carcinoma, and melanoma. For a detailed discussion of such applications, for example, see, Garon et al. "In Vitro and In Vivo Evaluation and a Case Report of Intense Nanosecond Pulsed Electric Field as a Local Therapy for Human Malignancies", Int. J. Cancer, vol. 121, 2007, pages 675-682. The entire content of this publication is incorporated herein by reference.

The voltage induced across a cell membrane may depend on the pulse length and pulse amplitude. Pulses longer than about 1 microsecond may charge the outer cell membrane and lead to opening of pores, either temporarily or permanently. Permanent openings may result in cell death.

Pulses shorter than about 1 microsecond may affect the cell interior without adversely or permanently affecting the outer cell membrane. Such shorter pulses with a field strength varying in the range of 10 kV/cm to 100 kV/cm may trigger apoptosis (i.e. programmed cell death). These higher electric field strengths and shorter electric pulses may be useful in manipulating intracellular structures, such as nuclei and mitochondria.

Nanosecond high voltage pulse generators have been proposed for biological and medical applications. For example, see: Gundersen et al. "Nanosecond Pulse Generator Using a Fast Recovery Diode", IEEE 26.sup.th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Yampolsky et al., "Repetitive Power Pulse Generator With Fast Rising Pulse" U.S. Pat. No. 6,831,377; Schoenbach et al. "Method and Apparatus for Intracellular Electro-Manipulation", U.S. Pat. No. 6,326,177; Gundersen et al., "Method for Intracellular Modifications Within Living Cells Using Pulsed Electric Fields", U.S. Patent Application No. 2006/0062074; Kuthi et al., "High Voltage Nanosecond Pulse Generator Using Fast Recovery Diodes for Cell Electro-Manipulation", U.S. Pat. No. 7,767,433; Krishnaswamy et al., "Compact Subnanosecond High Voltage Pulse Generation System for Cell Electro-Manipulation", U.S. Patent Application No. 2008/0231337; and Sanders et al. "Nanosecond Pulse Generator", U.S. Patent Application No. 2010/0038971. The entire content of these publications is incorporated herein by reference.

SUMMARY

This disclosure relates to an in vivo treatment of a skin lesion of a mammal comprising application of electrical energy to the skin lesion in the form of one or more electrical pulses. The pulse duration may be at least 0.01 nanoseconds (ns) at the full-width-half-maximum (FWHM). The pulse duration may also be at least 1 ns at FWHM. Or the pulse duration may be at least 5 ns at FWHM. The pulse duration may be 1,000 ns or shorter at FWHM. This treatment may at least prevent growth of the lesion.

The phrase skin lesion, as used herein, is any deviation of skin from a healthy or a normal condition. Examples of skin lesions are skin diseases, conditions, injuries, defects, abnormalities or combinations thereof. For example, such skin lesions include malignancies (such as basal cell carcinomas, squamous cell carcinomas and melanoma), precancerous lesions (such as actinic keratosis), human papilloma virus (HPV) infected cells (such as verruca vulgaris or common warts, plantar warts, genital warts), immune-related conditions (such as psoriasis), other skin abnormalities (such as seborrheic keratosis and acrocordon), or combinations thereof. In one embodiment, the skin lesion is basal cell carcinoma (including papilloma), squamous cell carcinoma, actinic keratosis, warts, or combinations thereof. The skin lesion may also include aged skin, wrinkled skin or damaged skin. An example of the damaged skin is the skin damaged by sun radiation.

This treatment may at least prevent growth of the skin lesion for a duration of one week after the treatment. This treatment may reduce the skin lesion volume by at least 50% within one week after the treatment. This treatment may clear the lesion within one week after the treatment for at least 50% of cases.

The duration of the pulse at FWHM may be in the range of 0.01 ns to 1,000 ns. The duration of the pulse at FWHM may also be in the range of 1 ns to 100 ns, or in the range of 1 ns to 30 ns.

The applied electrical energy per volume of the skin lesion may be at least 10 mJ/mm$^3$ or at least 100 mJ/mm$^3$ or at least 1,000 mJ/mm$^3$. The applied electrical energy per volume of the skin lesion may also be in the range of 10 mJ/mm$^3$ to 10,000 mJ/mm$^3$.

The electrical field produced by each pulse may be at least 1 kV/cm at the peak amplitude of the pulse. The electrical field produced by each pulse may also be at least 10 kV/cm at the peak amplitude of the pulse. The electrical field produced by each pulse may be in the range of 1 kV/cm to 1,000 kV/cm at the peak amplitude of the pulse. The electrical field produced by each pulse may be in the range of 10 kV/cm to 100 kV/cm at the peak amplitude of the pulse.

The number of electrical pulses during a single treatment may be at least 10. The number of pulses may also be at least 100. Yet, the number of pulses may be at least 1,000. The number of pulses may be less than 10,000.

In one embodiment, this treatment may be an in vivo treatment of a skin lesion of a human comprising at least one treatment session, i.e. administration of the electrical energy to the skin lesion by physician at an office visit. The at least one treatment session may comprise applying electrical energy to the skin lesion of the human comprising delivering at least one electrical pulse with a pulse duration at FWHM in the range of 0.01 ns to 1,000 ns, forming an electrical field in the lesion, and thereby at least preventing growth of the lesion. This pulse duration at FWHM may also be in the range of 1 ns to 100 ns, or in the range of 1 ns to 30 ns.

In this embodiment, the skin lesion of a human may be any deviation of skin from a healthy condition. The skin lesion may also be malignancies, precancerous lesions, human papilloma virus (HPV) infected cells, immune-related conditions, seborrheic keratosis, acrocordon, or combinations thereof. The skin lesion may also include aged skin, wrinkled skin or damaged skin. An example of the damaged skin is the skin damaged by sun radiation. The skin lesion may be basal cell carcinoma, squamous cell carcinoma, actinic keratosis, warts, or combinations thereof. The skin lesion may be common warts, actinic keratosis or combinations thereof. The skin lesion may be actinic keratosis.

In this embodiment, the pulse duration at FWHM may be in the range of 0.01 ns to 1,000 ns; or in the range of 1 ns to 100 ns, or in the range of 1 ns to 30 ns. The electrical field formed by each pulse at the peak amplitude of the pulse may be at least 1 kV/cm; at least 10 kV/cm; in the range of 1 kV/cm to 1,000 kV/cm; or in the range of 10 kV/cm to 100 kV/cm. Applying electrical energy may comprise applying at least 10 pulses during a treatment, at least 100 pulses, or at least 1,000 pulses. The applied electrical energy per volume of the skin lesion may be at least 10 mJ/mm$^3$, at least 100 mJ/mm$^3$, at least 1,000 mJ/mm$^3$, or in the range of 10 mJ/mm$^3$ to 10,000 mJ/mm$^3$.

In one embodiment, the skin lesion of the human may be common warts. In this embodiment, the applied electrical energy per volume of the skin lesion may be at least 920 mJ/mm$^3$ to at least prevent growth of the warts. The wart treatment may induce at least 21% shrinkage of the wart, or at least 40% shrinkage of the wart, or at least 70% shrinkage of the wart. Common warts may also be cleared by this treatment. This treatment may at least prevent the growth of the warts. And the at least prevention of the wart growth may last at least 41 days.

In another embodiment, the skin lesion of the human may be actinic keratosis. For this treatment, the applied electrical energy per volume of the skin lesion may be at least 473 mJ/mm$^3$ to at least prevent growth of the actinic keratoses. This treatment may be carried out to induce at least 20% shrinkage of the actinic keratosis, or at least 40% shrinkage of the actinic keratosis, or at least 70% shrinkage of the actinic keratosis. This treatment may also be carried out to clear actinic keratoses. This treatment may at least prevent growth of the actinic keratoses. And the at least prevention of the actinic keratosis growth may last at least 56 days.

The treatment of a human lesion may also comprise a plurality of treatment sessions. For example, it may comprise at least two treatment sessions or at least three treatment sessions.

The system used for the treatment of the skin lesion may include an applicator tip that comprises at least one delivery electrode and at least one ground electrode.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

DETAILED DESCRIPTION OF ILLUSTRATIVE EMBODIMENTS

Figure 1:
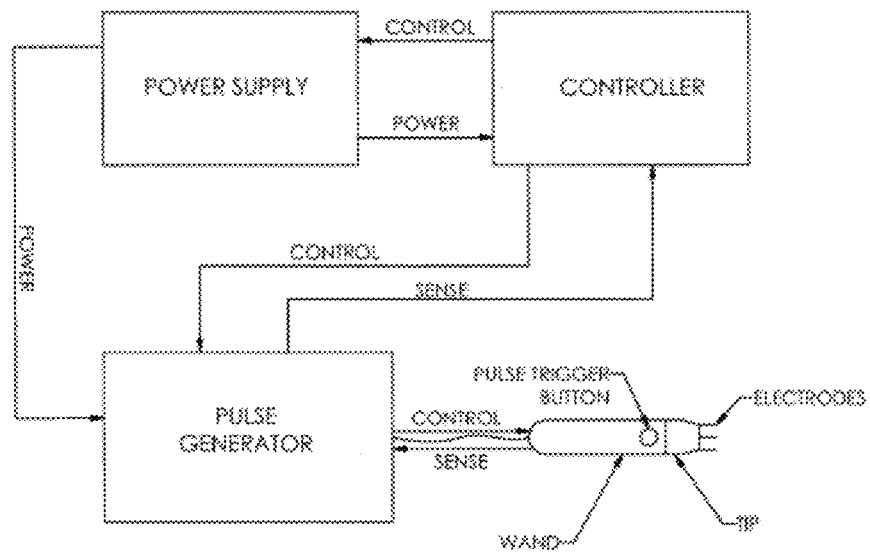
FIG. 1: Example of a system for generation and delivering electrical nanopulses to a skin lesion.

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

This disclosure relates to an in vivo treatment of skin lesions of mammals by application of electrical pulses with duration of 1,000 nanoseconds (ns) or less as measured at the full-width-at-half-maximum (FWHM) of the pulse wave.

The skin lesion that may be treated in vivo by the devices described herein may be any deviation of skin from a healthy or a normal condition. Examples of the skin lesions include skin diseases, conditions, injuries, defects, abnormalities or combinations of thereof. For example, such skin lesions may be malignancies (such as basal cell carcinomas, squamous cell carcinoma and melanoma), precancerous lesions (such as actinic keratosis), human papilloma virus (HPV) infected cells (such as verruca vulgaris or common warts, plantar warts, genital warts), immune-related conditions (such as psoriasis), other skin abnormalities (such as seborrheic keratosis and acrocordon) and combinations thereof. The skin lesion may also include aged skin, wrinkled skin or damaged skin. An example of the damaged skin is the skin damaged by sun radiation. In one embodiment, the skin lesions may be basal cell carcinoma (including papilloma), squamous cell carcinoma, actinic keratosis, warts, or combinations thereof. In one embodiment, the skin lesion may be a skin lesion of a human. In this embodiment, the skin lesion may comprise basal cell carcinoma, squamous cell carcinoma, actinic keratosis, warts, or combinations thereof. In this embodiment, the skin lesion may also comprise common warts, actinic keratosis, or combinations thereof. The skin lesion may be a common wart of a human. The skin lesion may also be an actinic keratosis of a human.

The in vivo treatment may be achieved by providing electrical energy to the skin lesion in a form of one or more electrical pulses. During this treatment, tissue removal may not be intentional and, if it happens, may not be substantial. Thus, the treatment may thereby be advantageous over current or other proposed treatment techniques, since it may achieve its purpose with no substantial tissue removal.

The in vivo treatment of the skin lesion may at least prevent growth of the lesion. In one embodiment, the treatment may reduce the volume of the skin lesion. That is, the treatment induces at least shrinkage of the lesion. This shrinkage may be at least 10%, 20%, 30%, 60%, 70%, 80%, 90%, or more than 90%. Yet, in another embodiment, it may be a treatment to reduce the skin lesion volume to a negligible level (i.e. clearance of the lesion). Yet, in other embodiments, the lesion growth prevention or the lesion volume reduction may be achieved in at least 10%, 20%, 30%, 40%, 50%, 60%, 70%, 80%, 90%, or more than 90% of cases.

When the lesion volume shrinks to a negligible size (i.e. about 100%), the lesion is "cleared". If the lesion growth or shrinkage is less than 10% after the treatment, the lesion growth is considered to have been "prevented" or that there is "no change". If the lesion shrinkage is in the range of >10% and <50%, it is concluded that there is lesion "shrinkage". If the lesion shrinkage is in the range of >50% and <100%, it is concluded that there is "substantial shrinkage". If the lesion growth is in the range of >10% to <100%, it is concluded that there is lesion "growth". And if the lesion growth is >100%, it is concluded that there is "substantial growth".

If the height (i.e. protrusion) of the lesion above the skin surface is negligibly small, i.e. about 0.00 mm, the lesion height is recorded as about 0.10 mm.

The treatment results may be permanent or temporary. In one embodiment, the growth prevention, or the shrinkage or the clearance may last for a duration of at least 7 days, at least 10 days, at least 20 days, at least 30 days, at least 40 days, at least 50 days, at least 60 days, at least 70 days, at least 80 days, at least 90 days, at least 100 days, or at least 110 days.

In one embodiment, the treatment comprises at least one treatment session. For example, the treatment session may comprise an administration of the electrical energy to the skin lesion of a human by physician at an office visit. The treatment of a human lesion may also comprise a plurality of treatments sessions. For example, it may comprise at least two treatment sessions or at least three treatment sessions.

Furthermore, these electrical nanopulse treatments may be combined with any other treatment to increase efficacy of the lesion treatment. These other treatments may include over-the-counter treatments, treatments with prescription medicines, surgery, and destructive procedures. For example, these other lesion treatments may include curettage, electrodessication, cryotherapy, topical therapy, and combinations thereof.

Any system suitable for delivery of electrical nanopulses with a duration of 1,000 ns or less at FWHM to the skin lesion may be used.

The system may comprise a power supply, a controller, a pulse generator, and a pulse delivery device (e.g., a wand). An example of this system is schematically shown in FIG. 1.

The pulse generator may be any pulse generator that is capable of generating pulses with a duration of 1,000 ns or less at FWHM. Examples of such pulse generators are disclosed in Kuthi et al., "High Voltage Nanosecond Pulse Generator Using Fast Recovery Diodes for Cell Electro-Manipulation", U.S. Pat. No. 7,767,433; Sanders et al. "Nanosecond Pulse Generator", U.S. Patent Application No. 2010/0038971; and Schoenbach et al. "Method and Apparatus for Intracellular Electro-Manipulation", U.S. Pat. No. 6,326,177. The content of these publications are incorporated herein by reference.

The pulse delivery device may be any device that can deliver electrical pulses to the skin lesion. This device may have an applicator tip that may comprise at least one delivery electrode. This applicator may further comprise at least one ground electrode. In one embodiment, the delivery electrode and/or the ground electrode may penetrate into the skin lesion to deliver the electrical pulses. In another embodiment, the delivery electrode and/or the ground electrode may deliver the electrical pulses without substantially or intentionally penetrating into the skin lesion. For example, the skin lesion may be constricted between the electrodes or the electrodes may only touch the lesion during the delivery of the electrical pulses.

Figure 4:
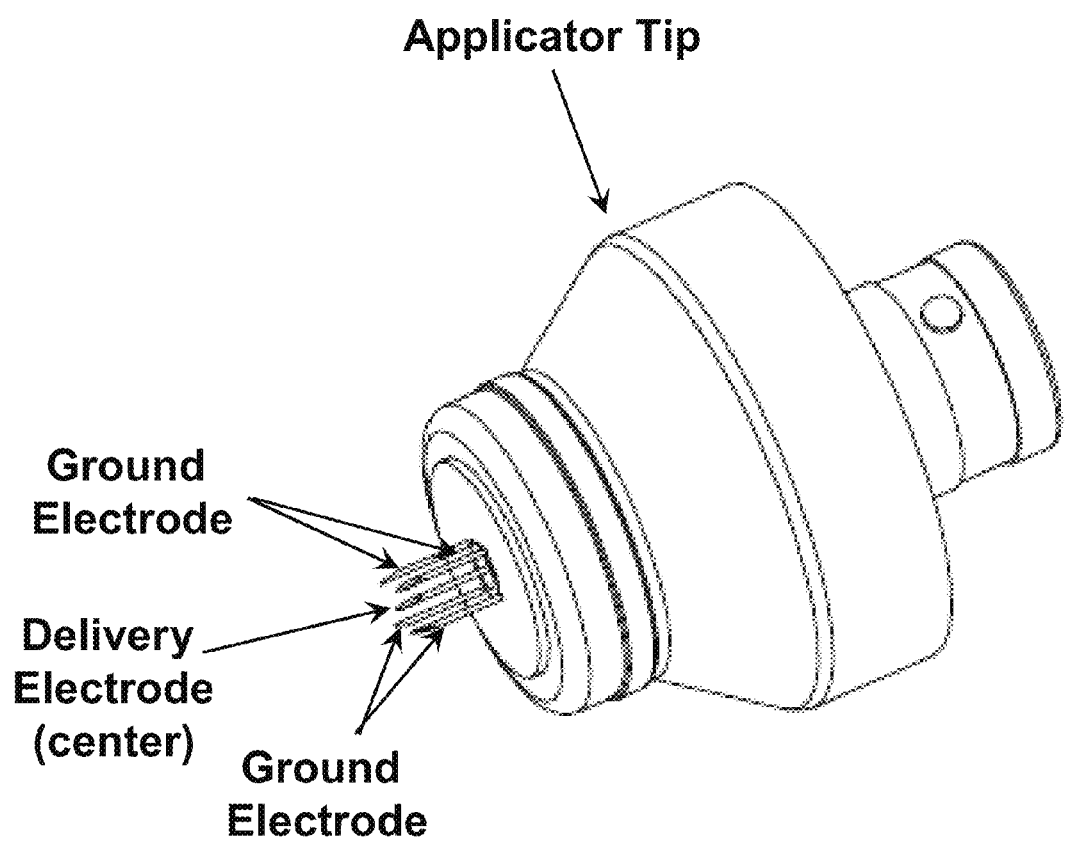
FIG. 4: Example of an applicator tip with one delivery electrode and four ground electrodes.

An example of the applicator tip is illustrated in FIG. 4. In this example, the applicator tip has one delivery electrode placed at the center and four ground electrodes surrounding the delivery electrode. The base of the electrodes may be embedded in a solid insulating material to maintain separations between them.

The electrical energy may be applied to the skin lesion in the form of at least one electrical pulse. In one embodiment, at least 10 pulses, at least 100 pulses or at least 1,000 pulses may be applied to treat the lesion during a single treatment.

In one embodiment, the duration of one or more of the pulses at FWHM may be in the range of 0.01 ns to 1,000 ns. The duration of one or more of the pulses at FWHM may also be in the range of 1 ns to 100 ns or in the range of 1 ns to 30 ns.

Total electrical energy applied per volume of skin lesion may be at least 10 mJ/mm$^3$, at least 20 mJ/mm$^3$, at least 100 mJ/mm$^3$, at least 500 mJ/mm$^3$, or at least 1,000 mJ/mm$^3$. In another embodiment, the total applied electrical energy per volume of the skin lesion may be in the range of 10 mJ/mm$^3$ to 10,000 mJ/mm$^3$.

The electrical field produced by each pulse may be at least 1 kV/cm at the peak amplitude of the pulse. The electrical field produced by each pulse may also be at least 10 kV/cm at the peak amplitude of the pulse. In another embodiment, the electrical field produced by each pulse may be in the range of 1 kV/cm to 1,000 kV/cm at the peak amplitude of the pulse. Yet, in another embodiment, the electrical field produced by each pulse may be in the range of 10 kV/cm to 100 kV/cm at the peak amplitude of the pulse.

The treatment may comprise at least one treatment session, i.e. administration of the electrical energy to the skin lesion by physician at an office visit. This treatment session may comprise at least one application of the electric energy to a lesion. The electrical energy may be delivered to the skin lesion in any manner suitable for the skin lesion. For example, the electrical energy may be delivered after contacting the surface of the lesion by electrodes of the applicator tip. In this example, the electrodes don't penetrate into the lesion during the application of the electrical energy. In another example, the electric energy may also be delivered after insertion of the electrodes to the skin lesion. For example, one application may comprise first penetration of the skin lesion by the electrodes of the applicator tip and then delivery of about 100 pulses with a pulse duration of about 18 ns at FWHM. More than one application may be used per treatment session to treat the lesion. The number of applications may depend on the size and/or the type of the lesion. Larger lesions may require more than one application per treatment session, as discussed in detail below. Also, different types of lesions may require higher energies, and therefore more applications per treatment session may be needed to at least prevent the growth of the lesions. The treatment of a lesion may also comprise a plurality of treatment sessions. For example, it may comprise at least two treatment sessions or at least three treatment sessions. These treatment sessions may also be separated in time by 7 days or more.

Example 1

Nanopulse Generator and Electrical Nanopulses

An electrical pulse generation and delivery system, schematically shown in FIG. 1, comprising a pulse generator was constructed at the Alfred E. Mann Institute for Biomedical Engineering at the University of Southern California (Los Angeles, Calif.).

Figure 2:
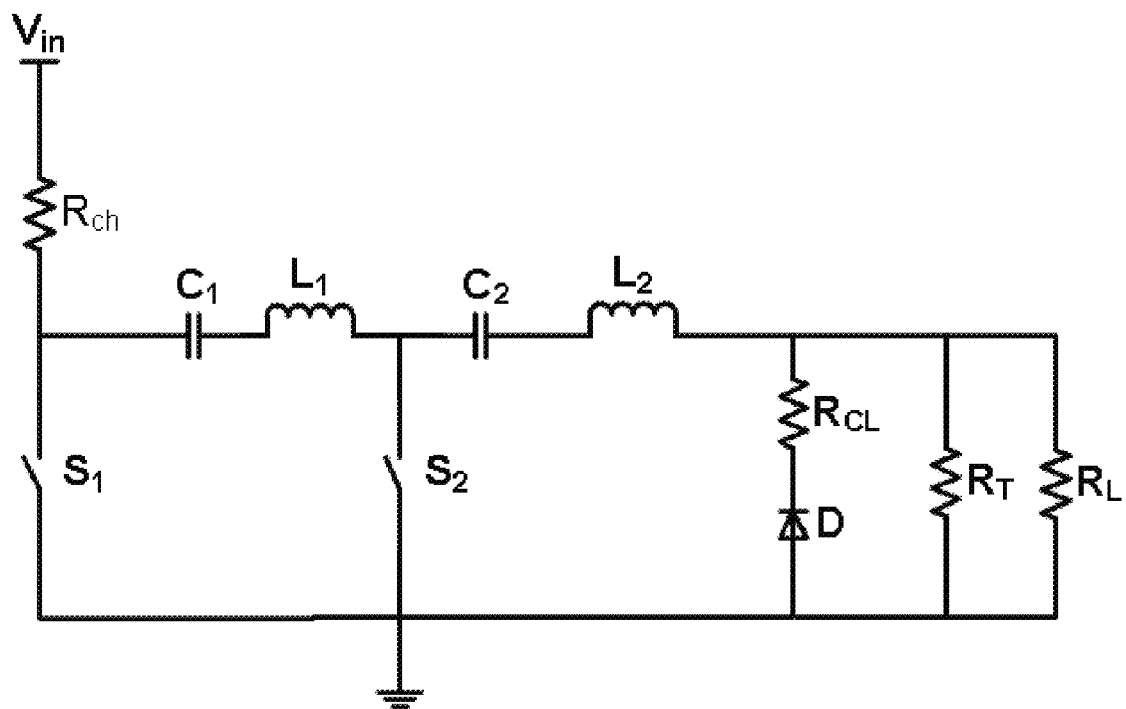
FIG. 2: Example of a simplified diode pulse generator.

An example of the pulse generator is schematically shown in FIG. 2. This pulse generator was previously disclosed in detail in U.S. Pat. No. 7,767,433 to Kuthi et al. and in U.S. Patent Application U.S. 2010/0038971 to Sanders, the content of which is incorporated by reference. This pulse generator is briefly described below:

As shown in FIG. 2, the diode pulse generator may include a tank circuit consisting of inductances $L_1$ and $L_2$ and capacitances $C_1$ and $C_2$. The tank circuit may be connected in series with a diode D across which a load $R_L$ to be driven may be connected. This load may be the resistance of the lesion or tissue. The pulse generator may include a switching system, such as switches $S_1$ and $S_2$, which may be electronic. A voltage supply $V_{in}$ may be connected to the diode pulse generator through a resistance $R_{ch}$.

Before the beginning of a pulse cycle, the switch $S_1$ may be open and the switch $S_2$ may be closed. This may cause the capacitance $C_1$ to fully charge and the capacitance $C_2$ to fully discharge.

At the beginning of the pulse cycle, the switch $S_1$ may be closed and the switch $S_2$ may be opened. This may cause charge to transfer from the capacitance $C_1$ to the capacitance $C_2$. During this transfer, the current through the tank circuit may rise and fall in approximately a sinusoidal manner.

This current may cause the diode D to be forward-biased as it travels travel through it. During this process, charge may be stored in the depletion layer of the diode D.

At the end of the half-cycle, switch $S_2$ may be closed. During the next half-cycle, the current flow may reverse in direction, causing the diode D to be reverse-biased. During the first part of the second half-cycle, current may still flow through the diode D while charge in its depletion layer is being depleted. Once the charge is depleted, the current through the diode D stops, causing the diode to appear as an open switch. This may cause the current through the inductance $L_2$ to commute from the diode D to the load $R_L$. The diode D may thus be configured to act as an opening switch, interrupting the current in the inductance $L_2$ and commuting it into the load $R_L$.

Current may now travel through the load $R_L$ until the energy stored in the tank circuit consisting of the capacitance $C_2$ and the inductance $L_2$ depletes, thus delivering a pulse into the load $R_L$.

This pulse generator included a current limiting resistor, $R_{CL}$ configured to limit damage to the pulse generator. The value of this resistor was about 1 ohm. The pulse generator further included a terminating resistance, $R_T$ in parallel with the diode, wherein the terminating resistance was configured to protect the output stage of the pulse generator. The value of this resistor was about 100 ohms.

Figure 3:
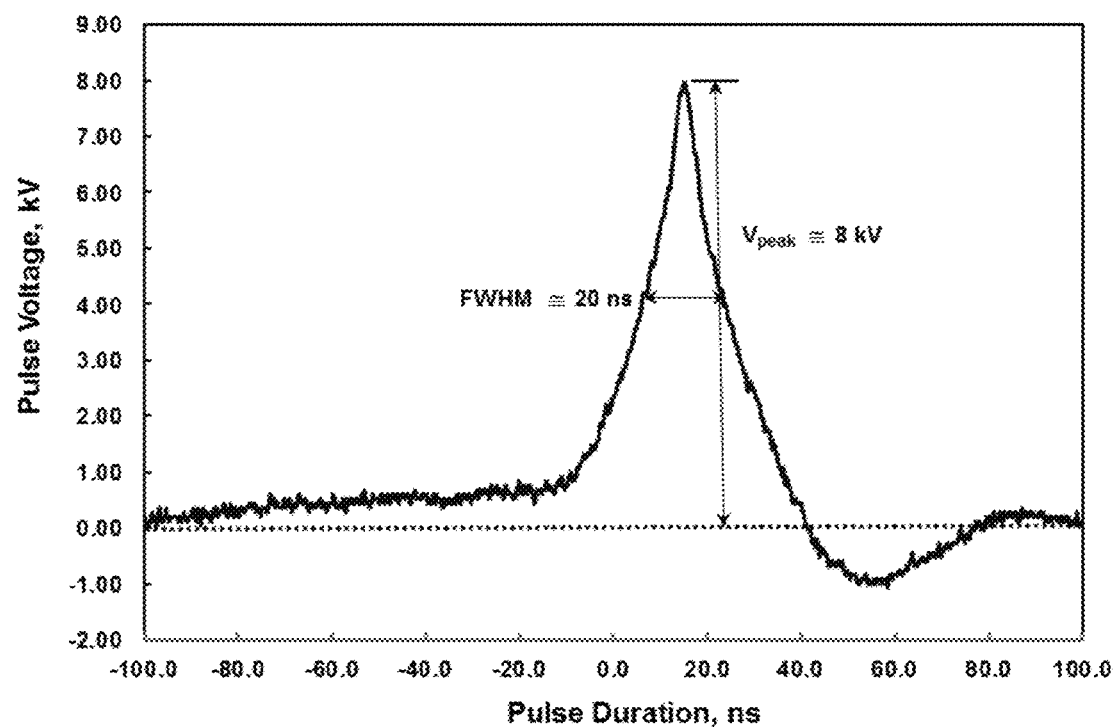
FIG. 3: Example of an electrical pulse generated by the system shown in FIG. 1.

The pulse generator disclosed above provided at least one electrical pulse with a duration varying in the range of about 7 nanoseconds (ns) at FWHM to about 20 ns at FWHM. In one example, a pulse with duration of about 20 ns at FWHM was generated. The characteristics of this pulse were recorded by an oscilloscope manufactured by Tektronix (Beaverton, Oreg.) with a model number of DPO4104. As shown in FIG. 3, this pulse had pulse duration of about 20 ns at FWHM and a peak amplitude of about 8.00 kV.

The electrical nanopulses were delivered to a lesion by using applicator tips comprising one delivery electrode and four ground electrodes surrounding the delivery electrode. This applicator tip is shown in FIG. 4. Each electrode was constructed by using a 30 gauge needle (i.e. about 0.255 mm in diameter). The delivery and the ground electrodes have the same the length for each applicator tip. This length varied in the range of about 2 millimeters (mm) to 5 mm. The electrodes were placed to form a square pattern. The ground electrodes were at the corners of this square and the delivery electrode was at its center. Center-to-center distance between the delivery electrode and each ground electrode was about 1.75 mm. This configuration provided a volume of about 30.625 cubic-millimeters ($mm^3$) within the boundary formed by ground electrodes. The ground electrodes and the delivery electrode were electrically isolated from each other by embedding them in a Teflon insulation (not shown in FIG. 4).

The tip configuration may be different than illustrated. There may be other applicator tip configurations suitable for the treatment of the lesions. These configurations may include tips comprising at least one delivery electrode and at least one ground electrode. For example, as the system disclosed above is coaxial in nature, with the ground electrodes surrounding the delivery electrode, any number of needle configurations may be realized, including a circular arrangement with five or more ground electrodes, a triangular arrangement with three ground electrodes, wherein the delivery electrode may be placed at the geometrical center of such arrangements. A simple linear arrangement with just two opposing electrodes, i.e., one return electrode and one delivery electrode, may also be used for the delivery of the electrical pulses.

Still other tip configurations, for example those with different electrode spacing or length, may also be used for the treatment of the lesions. However, as the effect of these short pulses on cells is largely dependent upon the strength of electric field, an increase in return and active electrode spacing may have to be accompanied by a proportional increase in output voltage to maintain the required field for the effect on cells. Similarly, if the spacing is reduced, the voltage could be proportionally decreased.

Each pulse with a duration of about 7 ns at FWHM contained significant frequency components centered at about 142.9 megahertz (MHz), and each pulse with a duration of about 14 ns at FHWM contained significant frequency components centered at about 71.4 MHz. Electrical nanopulses with two different amplitudes, one with a peak amplitude of about 7.0 kilovolts (kV) and other with a peak amplitude of about 5.5 kV, were generated with a frequency of about 50 pulses per second. The electrical field was about 40 kilovolts/centimeter (kV/cm) at the peak amplitude of about 7.0 kV and about 31 kV/cm at the peak amplitude of about 5.5 kV.

Values of the pulse durations and the peak amplitudes disclosed in this document were average values unless specifically noted. These pulse durations and the peak amplitudes may vary with a standard deviation of 10% of their average values. For example, the pulse duration of about 7 ns at FWHM may be an average of pulse durations that vary within the range of 6.30 ns and 7.70 ns, or it is 7.00±0.70 ns.

Similarly, the peak amplitude of about 7.00 kV may be an average of the peak amplitudes that vary within the range of 6.30 kV and 7.70 KV, or it is 7.00±0.70 kV.

Electrical power delivered by the applicator tip at the peak of the pulse, $P_{peak}$ is:

$$P_{peak} = V^2_{peak}/R_L \quad \text{Equation 1}$$

where, $V_{peak}$ is peak amplitude of electrical potential. $R_L$ was fixed at about 100 ohms when the pulse generator was configured. That is, the lesion resistance was expected to be about 100 ohms.

And, the electrical energy delivered by the applicator tip per pulse, $E_p$ is:

$$E_p = (2 \times P_{peak} \times t_{FWHM})/3 \quad \text{Equation 2}$$

where, $t_{FWHM}$ is the pulse duration at FWHM.

Then, for $R_L$ of about 100 ohms and $V_{peak}$ of about 7.00 kV, the total energy delivered to the tissue per pulse was calculated to about 2.29 millijoules (mJ) for the pulse duration of about 7 ns at FWHM, about 4.57 mJ for the pulse duration of about 14 ns at FWHM, or about 5.88 mJ for the pulse duration of about 18 ns at FWHM. For $R_L$ of about 100 ohms and $V_{peak}$ of about 5.5 kV, the total energy delivered to the tissue per pulse was calculated to be about 2.82 mJ for the pulse duration of about 14 ns at FWHM Example 2

Mouse Model and Formation of Skin Lesions

All experiments with mice were conducted after experimental procedures were approved by Institutional Animal Care and Use Committee (IACUC) of Department of Comparative Medicine Cedars Sinai Medical Center, Santa Monica, Calif. For all procedures, mice were given isofluorane anesthesia and positioned on a warming bed.

Cutaneous papillomas and squamous carcinomas were chemically induced according to an established protocol disclosed in following publications: Hennings H, Shores R, Mitchell P, Spangler E F, Yuspa S H "Induction of papillomas with a high probability of conversion to malignancy" Carcinogenesis (1985) 6:1607-10; Hennings H, Spangler E F, Shores R, Mitchell P, Devor D, Shamsuddin A K, Elgjo K M, Yuspa S H "Malignant conversion and metastasis of mouse skin tumors: a comparison of SENCAR and CD-1 mice" Environmental health perspectives (1986) 68:69-74; and Slaga T J "SENCAR mouse skin tumorigenesis model versus other strains and stocks of mice" Environmental health perspectives (1986) 68:27-32. The entire content of these publications is incorporated herein by reference.

SENCAR (SENsitivity to CARcinogenesis) and CD-1 mice were used as model animals to induce tumors on their skin and to treat these tumors with electrical nanopulses. SENCAR mice were developed from CD-1 mice by recurrent selection of mice that are sensitive to chemically induced tumor development. SENCAR-A mice (SENCAR A/PtCr) were provided by National Cancer Institute, Frederick, Md. and SENCAR-C mice (SENCAR C/PtJ) were purchased from The Jackson Laboratory, Bar Harbor, Me. CD-1 mice were bought from Charles River Laboratories International Inc., Wilmington, Md. Both SENCAR and CD-1 mice were maintained in Cedars Sinai Medical Center's animal facility.

Carcinogen was applied on the flank of the shaven murine skin using a cotton-tipped applicator. Briefly, tumors were initiated using about two micromoles of methyl-N'-nitro-N-nitrosoguanidine (MNNG) on the first week followed by promotion of the tumor using about two micrograms of 12-O-tetradecanoylphorbol-13-acetate (TPA) which was applied weekly. After 16 to 30 weeks, two to eight tumors (papillomas or carcinomas) were visually detected on each mouse, characterized by rapid growth with elevated margins. These tumors were pink in color and bulbous in appearance.

Based on histology, size and appearance of lesions (i.e. tumors), about 30 of them were expected to be squamous cell carcinomas showing signs of invasiveness and about 70% were expected to be papillomas. The papillomas are similar to human hypertrophic actinic keratosis (AK). AK is earliest identifiable lesion that may eventually develop into an invasive squamous cell carcinoma (SCC). AK is also clinically quite common and diagnosed in about 14% of all visits to dermatologists. Tumor growth was monitored by measuring size of each tumor using a caliper. Morphology of induced tumors was periodically examined using standard histology.

Examples 3 to 59

Application of Nanosecond Electrical Pulses to Skin Lesions

In Examples 3 to 59, the tumors, which were formed on the mice skin by following the method in the manner of Example 2, were treated by using the nanopulse generator and the applicator tip disclosed in Example 1.

To avoid formation of air pockets between the electrodes, both the tumor and the electrodes were covered with Aquasonic 100 ultrasound transmission gel (Parker Laboratories Inc., Fairfield, N.J., USA). Electrical pulses with varying duration, amplitude and number were delivered to the skin lesion to determine effects of these pulse parameters on tumor treatment.

Figure 5:
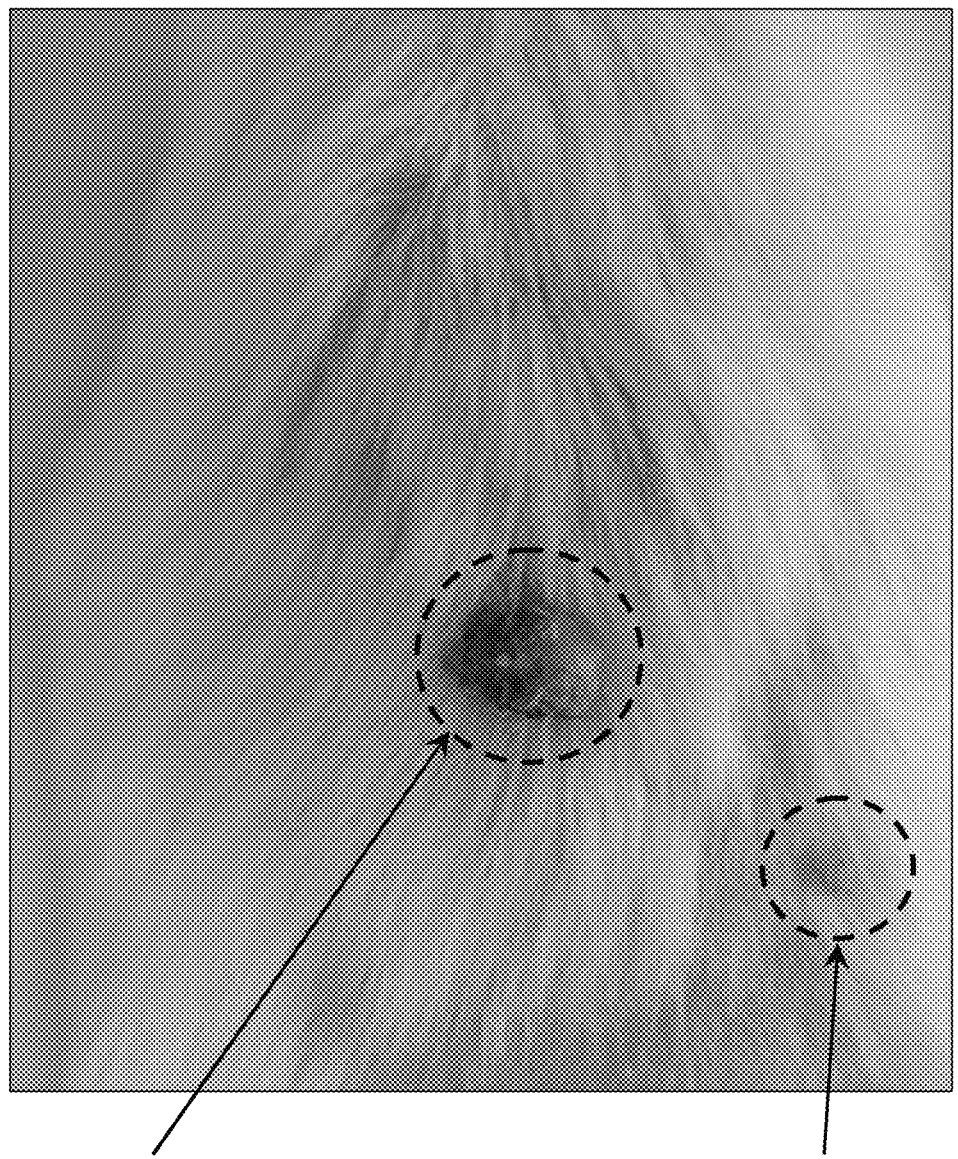
FIG. 5: Photograph of lesions on a mouse before a treatment.
Figure 6:
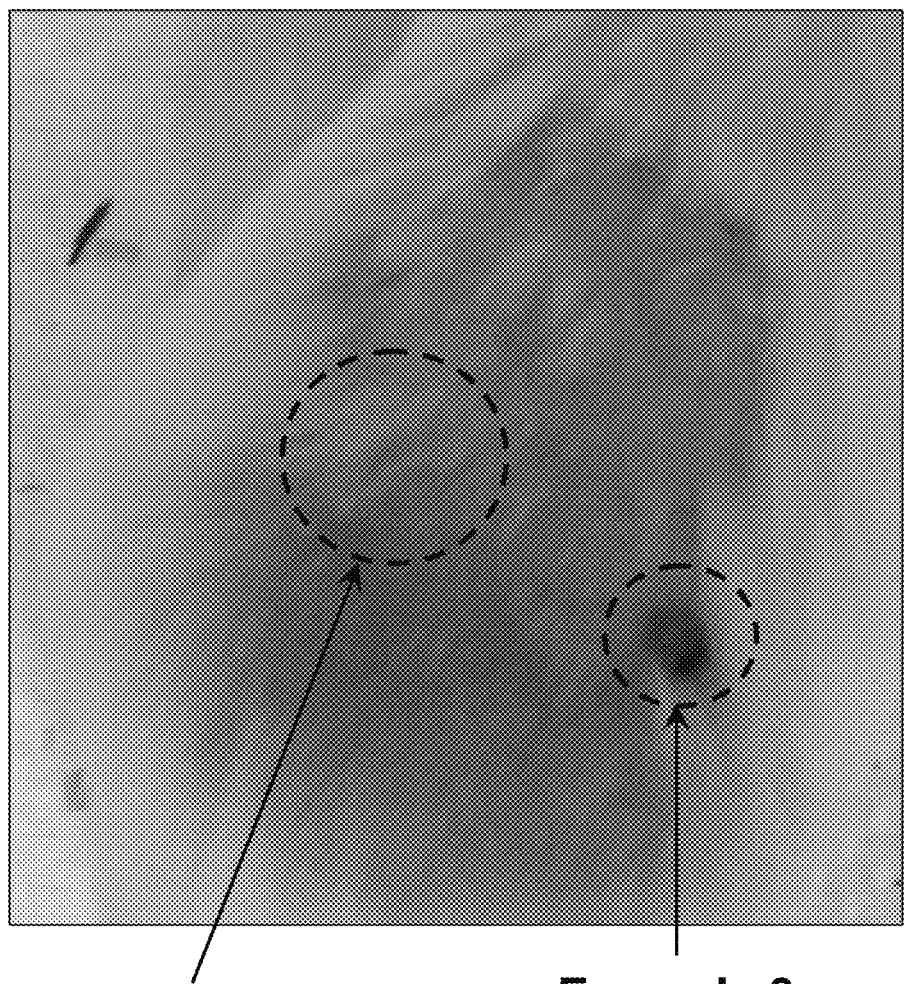
FIG. 6: Photograph of lesions on the mouse shown in FIG. 5 one week after the treatment.

Photographs of tumors were taken before and after each treatment and also one week after the treatment to record shape of the tumor, as shown in FIG. 5 and FIG. 6 by way of example.

Tumor size was measured before each treatment and one week after the treatment by using a vernier caliper. The highest elevation of the tumor as measured from the healthy skin surface was recorded as the tumor height. The longest length of the tumor as measured parallel to the healthy skin surface was recorded as the tumor length. For example, before the treatment, the size of the tumors shown in FIG. 5 were about 5.5 mm (length)×about 4 mm (width)×about 3 mm (height) in Example 36 and about 2.5 mm (length)×2.50 mm (width)×2.00 mm (height) in Example 3.

The widest size perpendicular to the tumor length was recorded as the tumor width. The tumor volume, $T_V$ was then calculated by using the following equation:

$$T_V = 0.625 \times T_L \times T_W \times T_H \quad \text{Equation 3}$$

where $T_L$ is the tumor length, $T_W$ is the tumor width and $T_H$ is the tumor height. The percent of tumor growth or shrinkage $T_C$ is:

$$T_C = 100 \times (T_{V,after} - T_{V,before})/T_{V,before} \quad \text{Equation 4}$$

where $T_{V,after}$ is the tumor volume measured one week after the treatment and $T_{V,before}$ is the tumor volume measured before the treatment.

For example, the volumes of the tumors shown in FIG. 5 were about 7.81 mm³ in Example 3 and about 41.25 mm³ in Example 36. As shown in FIG. 6 and summarized in Table 1, one week after the treatment, the tumor in Example 3 grew in volume by about 170%, as expected since this tumor was penetrated with the applicator tip but no electrical energy was applied to the tumor. And the tumor in Example 36 was cleared, i.e. its volume reduced by about 100%.

The pulse duration at FWHM, the pulse amplitude, and the number of pulses per application were set on the pulse generator. Then, the tumor was slightly elevated from the skin surface by inserting fingers gently under the tumor. Finally, the electrodes were vertically inserted into the tumor and the electrical pulses were applied. Great care was taken to prevent the electrodes from penetrating beyond the height of the tumor. Thus, during the application of the electrical pulses, the electrodes' distal ends were guided so that the electrodes did not penetrate deeper than the measured height of the tumor. For example, if the measured tumor height was about 3.00 mm, the penetration depth was also about 3.00 mm.

Surface of the tumors, facing the applicator tip, was generally round, but sometimes elliptical or elongated in shape. Locations for insertion of the delivery electrode were visually decided and evenly distributed on this surface. One application was carried out for each millimeter of the tumor length. Tumors shorter than one millimeter in length were not treated. For the tumors, which were longer than one millimeter but had lengths that were in fractions of a millimeter where the fractional length was in the range of 0.5 mm to 1.0 mm, the tumor length was rounded up to calculate the number of applications. For example, for the tumors that had lengths about 5.5 mm, 6 applications were carried out.

The center-to-center distance between two opposing ground electrodes was about 3.50 mm. For some tumors, this distance was wider than the width of these tumors. For these tumors, the ground electrodes partially penetrated into the tissue surrounding the tumor.

The total electrical energy delivered by the applicator tip per treatment, $E_T$ is:

$$E_T = E_P \times N_P \times A_N \qquad \text{Equation 5}$$

where $N_P$ is the number of pulses per application and $A_N$ is number of applications per tumor. Electrical energy delivered per volume of tumor, $E_V$ is:

$$E_V = E_T \times T_H / (N_H \times T_{V,before}) \qquad \text{Equation 6}$$

where $N_H$ is the electrode height, which was about 5 millimeters.

Results of experiments carried out to treat skin lesions of mice are summarized in Table 1 to 4. In these tables or tables following them, "−" sign in front of the numerals shown in the tumor growth/shrinkage column represent shrinkage of the lesion. For example, "−85%" means 85% shrinkage. If there is no "−" sign in front of the numerals shown in the tumor growth/shrinkage column, it represents growth of the lesion. For example, "43%" means 43% growth.

TABLE 1

Electrical pulses applied to skin lesions and treatment results.

| Example | Mouse Number | Tumor Number | Pulse Duration at FWHM (ns) | Peak Amplitude of Electrical Pulses (kV) | Electrical Energy Delivered Per Pulse (mJ) |
|---|---|---|---|---|---|
| 3 | SENCAR-C, 3 | 4 | 0 | 0.0 | 0.00 |
| 4 | CD-1, | 1 | 0 | 0.0 | 0.00 |
| 5 | SENCAR-C, 1 | 2 | 0 | 0.0 | 0.00 |
| 6 | CD-1, 2 | 1 | 0 | 0.0 | 0.00 |
| 7 | CD-1, 2 | 2 | 0 | 0.0 | 0.00 |
| 8 | SENCAR-C, 2 | 1 | 0 | 0.0 | 0.00 |
| 9 | 15 | 1 | 7 | 7.0 | 2.29 |
| 10 | 18 | 1 | 7 | 7.0 | 2.29 |
| 11 | 19 | 1 | 7 | 7.0 | 2.29 |
| 12 | 19 | 2 | 7 | 7.0 | 2.29 |
| 13 | 20 | 1 | 7 | 7.0 | 2.29 |
| 14 | 20 | 2 | 7 | 7.0 | 2.29 |
| 15 | 12 | 1 | 7 | 7.0 | 2.29 |
| 16 | 13 | 1 | 7 | 7.0 | 2.29 |
| 17 | 16 | 1 | 7 | 7.0 | 2.29 |
| 18 | 11 | 1 | 7 | 7.0 | 2.29 |
| 19 | 17 | 1 | 7 | 7.0 | 2.29 |
| 20 | 11 | 2 | 7 | 7.0 | 2.29 |
| 21 | 14 | 1 | 7 | 7.0 | 2.29 |
| 22 | CD-1 | 1 | 14 | 5.5 | 2.82 |
| 23 | 1, R | 1 | 14 | 5.5 | 2.82 |
| 24 | CD-1, 2 | 1 | 14 | 5.5 | 2.82 |
| 25 | CD-1, 3, R | 1 | 14 | 5.5 | 2.82 |
| 25 | SENCAR-C, 1 | 1 | 14 | 5.5 | 2.82 |
| 26 | CD-1, 1, L | 1 | 14 | 5.5 | 2.82 |
| 27 | SENCAR-C, 1-R | 2 | 14 | 7.0 | 4.57 |
| 28 | CD-1, 1-R | 1 | 14 | 7.0 | 4.57 |
| 29 | SENCAR-C, 1 | 1 | 14 | 7.0 | 4.57 |
| 30 | SENCAR-C, 1 | 2 | 14 | 7.0 | 4.57 |

TABLE 1-continued

Electrical pulses applied to skin lesions and treatment results.

| Example | Number of Electrical Pulses per Application | Number of Applications per Tumor | Total Electrical Energy Applied per Treatment (mJ) | Electrical Energy Applied per Tumor Volume (mJ/mm$^3$) |
|---|---|---|---|---|
| 3 | 0 | 3 | 0 | 0 |
| 4 | 0 | 4 | 0 | 0 |
| 5 | 0 | 3 | 0 | 0 |
| 6 | 0 | 3 | 0 | 0 |
| 7 | 0 | 3 | 0 | 0 |
| 8 | 0 | 3 | 0 | 0 |
| 9 | 50 | 3 | 344 | 18 |
| 10 | 50 | 6 | 687 | 9 |
| 11 | 50 | 3 | 344 | 18 |
| 12 | 50 | 5 | 573 | 7 |
| 13 | 50 | 3 | 344 | 18 |
| 14 | 50 | 5 | 573 | 9 |
| 15 | 100 | 3 | 687 | 29 |
| 16 | 100 | 3 | 687 | 24 |
| 17 | 100 | 6 | 1374 | 18 |
| 18 | 200 | 3 | 1374 | 49 |
| 19 | 200 | 6 | 2748 | 24 |
| 20 | 400 | 5 | 4580 | 73 |
| 21 | 400 | 5 | 4580 | 73 |
| 22 | 200 | 4 | 2256 | 60 |
| 23 | 200 | 3 | 1692 | 60 |
| 24 | 200 | 4 | 2256 | 60 |
| 25 | 200 | 3 | 1692 | 72 |
| 25 | 200 | 5 | 2820 | 45 |
| 26 | 200 | 4 | 2256 | 52 |
| 27 | 50 | 4 | 914 | 28 |
| 28 | 50 | 4 | 914 | 24 |
| 29 | 50 | 3 | 686 | 35 |
| 30 | 50 | 3 | 686 | 29 |

| Example | Tumor Size Before Treatment | | | | Tumor Size One Week After Treatment | | | |
|---|---|---|---|---|---|---|---|---|
| | Length (mm) | Width (mm) | Height (mm) | Volume (mm$^3$) | Length (mm) | Width (mm) | Height (mm) | Volume (mm$^3$) |
| 3 | 2.50 | 2.50 | 2.00 | 7.81 | 4.50 | 3.00 | 2.50 | 21.09 |
| 4 | 3.50 | 2.00 | 3.00 | 13.13 | 4.00 | 3.00 | 2.50 | 18.75 |
| 5 | 3.00 | 2.50 | 2.00 | 9.38 | 5.50 | 4.00 | 3.00 | 41.25 |
| 6 | 2.50 | 2.00 | 2.00 | 6.25 | 3.50 | 2.50 | 3.00 | 16.41 |
| 7 | 2.50 | 1.50 | 1.50 | 3.52 | 3.50 | 2.00 | 3.00 | 13.13 |
| 8 | 3.00 | 2.50 | 3.00 | 14.06 | 6.00 | 3.50 | 4.50 | 59.06 |
| 9 | 3.00 | 2.00 | 2.00 | 7.50 | 3.00 | 2.00 | 2.00 | 7.50 |
| 10 | 6.00 | 4.00 | 2.00 | 30.00 | 6.00 | 5.00 | 3.00 | 56.25 |
| 11 | 3.00 | 2.00 | 1.50 | 5.63 | 6.00 | 5.00 | 3.00 | 56.25 |
| 12 | 5.00 | 5.00 | 1.00 | 15.63 | 7.00 | 6.00 | 3.00 | 78.75 |
| 13 | 3.00 | 2.00 | 1.00 | 3.75 | 6.00 | 4.00 | 2.00 | 30.00 |
| 14 | 5.00 | 4.00 | 2.00 | 25.00 | 4.00 | 3.00 | 3.00 | 22.50 |
| 15 | 3.00 | 2.50 | 2.00 | 9.38 | 6.00 | 5.00 | 3.00 | 56.25 |
| 16 | 3.00 | 3.00 | 2.00 | 11.25 | 2.00 | 1.00 | 1.00 | 1.25 |
| 17 | 6.00 | 4.00 | 2.00 | 30.00 | 6.00 | 4.00 | 2.00 | 30.00 |
| 18 | 3.00 | 3.00 | 1.00 | 5.63 | 3.00 | 3.00 | 1.00 | 5.63 |
| 19 | 6.00 | 6.00 | 3.00 | 67.50 | 6.00 | 4.00 | 3.00 | 45.00 |
| 20 | 5.00 | 4.00 | 2.00 | 25.00 | 3.00 | 2.00 | 1.00 | 3.75 |
| 21 | 5.00 | 4.00 | 3.00 | 37.50 | 0.00 | 0.00 | 0.00 | 0.00 |
| 22 | 4.00 | 3.00 | 2.00 | 15.00 | 2.00 | 2.00 | 3.00 | 7.50 |
| 23 | 3.00 | 3.00 | 1.00 | 5.63 | 0.00 | 0.00 | 0.00 | 0.00 |
| 24 | 4.00 | 3.00 | 0.50 | 3.75 | 0.00 | 0.00 | 0.00 | 0.00 |
| 25 | 3.00 | 2.50 | 3.00 | 14.06 | 0.00 | 0.00 | 0.00 | 0.00 |
| 25 | 5.00 | 4.00 | 2.00 | 25.00 | 0.00 | 0.00 | 0.00 | 0.00 |
| 26 | 4.00 | 3.50 | 2.50 | 21.88 | 0.00 | 0.00 | 0.00 | 0.00 |
| 27 | 3.50 | 3.00 | 2.00 | 13.13 | 0.00 | 0.00 | 0.00 | 0.00 |
| 28 | 4.00 | 3.00 | 1.50 | 11.25 | 0.00 | 0.00 | 0.00 | 0.00 |
| 29 | 2.50 | 2.50 | 1.50 | 5.86 | 2.00 | 2.00 | 2.00 | 5.00 |
| 30 | 3.00 | 2.50 | 2.00 | 9.38 | 0.00 | 0.00 | 0.00 | 0.00 |

| Example | Tumor Growth or Shrinkage (%) | Conclusions |
|---|---|---|
| 3 | 170 | Tumor grew |
| 4 | 43 | Tumor grew |
| 5 | 340 | Tumor grew |
| 6 | 163 | Tumor grew |

TABLE 1-continued

Electrical pulses applied to skin lesions and treatment results.

| | | |
|---|---|---|
| 7 | 273 | Tumor grew |
| 8 | 320 | Tumor grew |
| 9 | 0 | Tumor volume not changed |
| 10 | 88 | Tumor grew |
| 11 | 900 | Tumor grew |
| 12 | 404 | Tumor grew |
| 13 | 700 | Tumor grew |
| 14 | −10 | Tumor shrunk |
| 15 | 500 | Tumor grew |
| 16 | −89 | Tumor shrunk |
| 17 | 0 | Tumor volume not changed |
| 18 | 0 | Tumor volume not changed |
| 19 | −33 | Tumor shrunk |
| 20 | −85 | Tumor shrunk |
| 21 | −100 | Tumor cleared |
| 22 | −50 | Tumor shrunk |
| 23 | −100 | Tumor cleared |
| 24 | −100 | Tumor cleared |
| 25 | −100 | Tumor cleared |
| 25 | −100 | Tumor cleared |
| 26 | −100 | Tumor cleared |
| 27 | −100 | Tumor cleared |
| 28 | −100 | Tumor cleared |
| 29 | −15 | Tumor shrunk |
| 30 | −100 | Tumor cleared |

| Example | Mouse Number | Tumor Number | Pulse Duration at FWHM (ns) | Peak Amplitude of Electrical Pulses (kV) | Electrical Energy Delivered Per Pulse (mJ) |
|---|---|---|---|---|---|
| 31 | SENCAR-C, 1 | 3 | 14 | 7.0 | 4.57 |
| 32 | SENCAR-C, 2 | 1 | 14 | 7.0 | 4.57 |
| 33 | SENCAR-C, 1 | 2 | 14 | 7.0 | 4.57 |
| 34 | SENCAR-C, 2 | 3 | 14 | 7.0 | 4.57 |
| 35 | SENCAR-C, 3 | 2 | 14 | 7.0 | 4.57 |
| 36 | SENCAR-C, 3 | 1 | 14 | 7.0 | 4.57 |
| 37 | SENCAR-C, 1 | 1 | 14 | 7.0 | 4.57 |
| 38 | SENCAR-C, 1 | 2 | 14 | 7.0 | 4.57 |
| 39 | SENCAR-C, 2 | 1 | 14 | 7.0 | 4.57 |
| 40 | SENCAR-C, 1 | 1 | 14 | 7.0 | 4.57 |
| 41 | CD-1, 1 | 1 | 14 | 7.0 | 4.57 |
| 42 | CD-1, 1 | 1 | 14 | 7.0 | 4.57 |
| 43 | SENCAR-C, 1 | 1 | 14 | 7.0 | 4.57 |
| 44 | SENCAR-C, 2 | 1 | 14 | 7.0 | 4.57 |
| 45 | SENCAR-C, 2 | 2 | 14 | 7.0 | 4.57 |
| 46 | CD-1, 2 | 1 | 14 | 7.0 | 4.57 |
| 47 | CD-1, 1 | 1 | 14 | 7.0 | 4.57 |
| 48 | CD-1, 1 | 1 | 14 | 7.0 | 4.57 |
| 49 | SENCAR-C, 3 | 3 | 14 | 7.0 | 4.57 |
| 50 | SENCAR-C, 2 | 3 | 14 | 7.0 | 4.57 |
| 51 | SENCAR-C, 3, R | 4 | 14 | 7.0 | 4.57 |
| 52 | SENCAR-C, | 1 | 14 | 7.0 | 4.57 |
| 53 | SENCAR-C | 1 | 14 | 7.0 | 4.57 |
| 54 | CD-1, 1 | 1 | 14 | 7.0 | 4.57 |
| 55 | CD-1, 3 | 1 | 14 | 7.0 | 4.57 |
| 56 | SENCAR-C, 3 | 2 | 14 | 7.0 | 4.57 |
| 57 | CD-1, 1 | 3 | 14 | 7.0 | 4.57 |
| 58 | CD-1, 1 | 2 | 14 | 7.0 | 4.57 |
| 59 | CD-1, 1, R | 1 | 14 | 7.0 | 4.57 |

| Example | Number of Electrical Pulses per Application | Number of Applications per Tumor | Total Electrical Energy Applied per Treatment (mJ) | Electrical Energy Applied per Tumor Volume (mJ/mm$^3$) |
|---|---|---|---|---|
| 31 | 50 | 5 | 1143 | 20 |
| 32 | 50 | 5 | 1143 | 18 |
| 33 | 200 | 6 | 5484 | 97 |
| 34 | 200 | 3 | 2742 | 117 |
| 35 | 200 | 5 | 4570 | 93 |
| 36 | 200 | 6 | 5484 | 80 |
| 37 | 200 | 2 | 1828 | 146 |
| 38 | 200 | 3 | 2742 | 117 |
| 39 | 200 | 3 | 2742 | 117 |
| 40 | 200 | 4 | 3656 | 97 |
| 41 | 200 | 5 | 4570 | 73 |
| 42 | 200 | 4 | 3656 | 84 |

TABLE 1-continued

Electrical pulses applied to skin lesions and treatment results.

| | | | | |
|---|---|---|---|---|
| 43 | 200 | 5 | 4570 | 108 |
| 44 | 200 | 2 | 1828 | 146 |
| 45 | 200 | 4 | 3656 | 111 |
| 46 | 400 | 4 | 7312 | 195 |
| 47 | 400 | 6 | 10968 | 146 |
| 48 | 400 | 2 | 3656 | 292 |
| 49 | 400 | 3 | 5484 | 390 |
| 50 | 400 | 3 | 5484 | 234 |
| 51 | 400 | 4 | 7312 | 223 |
| 52 | 400 | 5 | 9140 | 167 |
| 53 | 400 | 4 | 7312 | 223 |
| 54 | 400 | 4 | 7312 | 267 |
| 55 | 400 | 5 | 9140 | 146 |
| 56 | 400 | 4 | 7312 | 223 |
| 57 | 400 | 5 | 9140 | 162 |
| 58 | 400 | 4 | 7312 | 195 |
| 59 | 400 | 3 | 5484 | 195 |

| | Tumor Size Before Treatment | | | | Tumor Size One Week After Treatment | | | |
|---|---|---|---|---|---|---|---|---|
| Example | Length (mm) | Width (mm) | Height (mm) | Volume (mm$^3$) | Length (mm) | Width (mm) | Height (mm) | Volume (mm$^3$) |
| 31 | 4.50 | 4.00 | 3.50 | 39.38 | 0.00 | 0.00 | 0.00 | 0.00 |
| 32 | 5.00 | 4.00 | 3.00 | 37.50 | 0.00 | 0.00 | 0.00 | 0.00 |
| 33 | 6.00 | 3.00 | 3.00 | 33.75 | 0.00 | 0.00 | 0.00 | 0.00 |
| 34 | 3.00 | 2.50 | 2.00 | 9.38 | 0.00 | 0.00 | 0.00 | 0.00 |
| 35 | 4.50 | 3.50 | 2.00 | 19.69 | 0.00 | 0.00 | 0.00 | 0.00 |
| 36 | 5.50 | 4.00 | 3.00 | 41.25 | 1.50 | 1.50 | 0.00 | 0.00 |
| 37 | 2.00 | 2.00 | 1.50 | 3.75 | 0.00 | 0.00 | 0.00 | 0.00 |
| 38 | 3.00 | 2.50 | 2.00 | 9.38 | 0.00 | 0.00 | 0.00 | 0.00 |
| 39 | 3.00 | 2.50 | 1.00 | 4.69 | 0.00 | 0.00 | 0.00 | 0.00 |
| 40 | 4.00 | 3.00 | 1.00 | 7.50 | 0.00 | 0.00 | 0.00 | 0.00 |
| 41 | 5.00 | 4.00 | 3.00 | 37.50 | 0.00 | 0.00 | 0.00 | 0.00 |
| 42 | 4.00 | 3.50 | 4.00 | 35.00 | 0.00 | 0.00 | 0.00 | 0.00 |
| 43 | 4.50 | 3.00 | 2.50 | 21.09 | 0.00 | 0.00 | 0.00 | 0.00 |
| 44 | 2.00 | 2.00 | 2.00 | 5.00 | 0.00 | 0.00 | 0.00 | 0.00 |
| 45 | 3.50 | 3.00 | 2.50 | 16.41 | 0.00 | 0.00 | 0.00 | 0.00 |
| 46 | 4.00 | 3.00 | 3.00 | 22.50 | 0.00 | 0.00 | 0.00 | 0.00 |
| 47 | 6.00 | 4.00 | 2.00 | 30.00 | 0.00 | 0.00 | 0.00 | 0.00 |
| 48 | 2.00 | 2.00 | 2.00 | 5.00 | 0.00 | 0.00 | 0.00 | 0.00 |
| 49 | 3.00 | 1.50 | 2.00 | 5.63 | 0.00 | 0.00 | 0.00 | 0.00 |
| 50 | 3.00 | 2.50 | 2.00 | 9.38 | 0.00 | 0.00 | 0.00 | 0.00 |
| 51 | 3.50 | 3.00 | 1.50 | 9.84 | 0.00 | 0.00 | 0.00 | 0.00 |
| 52 | 5.00 | 3.50 | 3.00 | 32.81 | 0.00 | 0.00 | 0.00 | 0.00 |
| 53 | 3.50 | 3.00 | 2.00 | 13.13 | 0.00 | 0.00 | 0.00 | 0.00 |
| 54 | 3.50 | 2.50 | 3.00 | 16.41 | 2.50 | 1.50 | 1.50 | 3.52 |
| 55 | 5.00 | 4.00 | 3.00 | 37.50 | 0.00 | 0.00 | 0.00 | 0.00 |
| 56 | 3.50 | 3.00 | 1.50 | 9.84 | 0.00 | 0.00 | 0.00 | 0.00 |
| 57 | 4.50 | 4.00 | 3.00 | 33.75 | 0.00 | 0.00 | 0.00 | 0.00 |
| 58 | 4.00 | 3.00 | 2.50 | 18.75 | 0.00 | 0.00 | 0.00 | 0.00 |
| 59 | 3.00 | 3.00 | 2.00 | 11.25 | 0.00 | 0.00 | 0.00 | 0.00 |

| Example | Tumor Growth or Shrinkage (%) | Conclusions |
|---|---|---|
| 31 | −100 | Tumor cleared |
| 32 | −100 | Tumor cleared |
| 33 | −100 | Tumor cleared |
| 34 | −100 | Tumor cleared |
| 35 | −100 | Tumor cleared |
| 36 | −100 | Tumor cleared, scab remained |
| 37 | −100 | Tumor cleared |
| 38 | −100 | Tumor cleared |
| 39 | −100 | Tumor cleared |
| 40 | −100 | Tumor cleared |
| 41 | −100 | Tumor cleared |
| 42 | −100 | Tumor cleared |
| 43 | −100 | Tumor cleared |
| 44 | −100 | Tumor cleared |
| 45 | −100 | Tumor cleared |
| 46 | −100 | Tumor cleared |
| 47 | −100 | Tumor cleared |
| 48 | −100 | Tumor cleared |
| 49 | −100 | Tumor cleared |
| 50 | −100 | Tumor cleared |
| 51 | −100 | Tumor cleared |

TABLE 1-continued

Electrical pulses applied to skin lesions and treatment results.

| 52 | −100 | Tumor cleared |
| 53 | −100 | Tumor cleared |
| 54 | −79 | Tumor shrunk |
| 55 | −100 | Tumor cleared |
| 56 | −100 | Tumor cleared |
| 57 | −100 | Tumor cleared, scab remained |
| 58 | −100 | Tumor cleared, scab remained |
| 59 | −100 | Tumor cleared |

In Examples 3 to 8, no electricity was applied. That is, all electrical pulse generator parameters, the pulse duration, the amplitude and the number of electrical pulses per application were set at zero. Only the applicator tip was inserted into the tumor as described above. As expected, the tumors grew in the range of 43% to 340%. In Example 3, no electricity was applied, although the tip was inserted into the tumor shown in FIG. 5. As shown in FIG. 6, this tumor grew in size one week after the treatment and the volume growth was about 170%. These experiments demonstrated that in the absence of electrical nanopulses, the tumor growth is not prevented by only mechanical penetration of the electrodes.

After the first day following the treatment with electrical nanopulses, the tumors became noticeably darkened, nearly black in some places. This dark hue persisted for about 5 days, after which the color changed to pink and then returned to normal skin color. When the tumor volume shrunk to a negligibly measurable size (i.e. about 100%), this shrinkage was recorded as "tumor cleared". For some tumors, a scab like formation remained although their volume was determined to be negligible one week after the treatment. These scabs were flatter in shape, rough and hard in texture, and red in color. For the scabs, the shrinkage was recorded as "tumor cleared, but scab remained". In some treatments, the tumors did not shrink, but at the same time, they did not grow; that is about 0%. Thus, the tumor growth was prevented. For these treatments, the results were recorded as "tumor volume not changed".

As shown in Table 2, when the electrical energy applied per tumor volume was in the range of about 7.3 mJ/mm³ to about 18.3 mJ/mm³, the effect of electrical nanopulses on the tumor growth was negligible except in Example 32. In this electrical energy range, in examples 10-13, the tumors continued to grow. In examples 9 and 17, the tumor growth was prevented. In Example 14, the tumor shrinkage was negligible. However, in Example 32, the tumor was cleared at the energy of about 18.3 mJ/mm³.

These examples summarized in Table 2 demonstrated that onset of electrical energy required for a successful treatment of skin lesions was about 18.3 mJ/mm³. Below this energy level, the treatment was not effective.

TABLE 2

Electrical pulses applied to skin lesions and treatment results.

| Example | Pulse Duration at FWHM (ns) | Peak Amplitude of Electrical Pulses (kV) | Number of Electrical Pulses per Application | Electrical Energy Applied per Tumor Volume (mJ/mm³) | Tumor Growth or Shrinkage (%) | Notes |
| --- | --- | --- | --- | --- | --- | --- |
| 9 | 7 | 7.00 | 50 | 18.3 | 0 | Tumor volume not changed |
| 10 | 7 | 7.00 | 50 | 9.2 | 88 | Tumor grew |
| 11 | 7 | 7.00 | 50 | 18.3 | 900 | Tumor grew |
| 12 | 7 | 7.00 | 50 | 7.3 | 404 | Tumor grew |
| 13 | 7 | 7.00 | 50 | 18.3 | 700 | Tumor grew |
| 14 | 7 | 7.00 | 50 | 9.2 | −10 | Tumor shrunk |
| 17 | 7 | 7.00 | 100 | 18.3 | 0 | Tumor volume not changed |
| 32 | 14 | 7.00 | 50 | 18.3 | −100 | Tumor cleared |

These examples summarized in Table 2 further demonstrated that the skin lesion treatment may be more effective at pulse duration of about 14 ns at FWHM than at a pulse duration of about 7 ns at FWHM. However, in Examples 9 and 17, at least the tumor growth was prevented at an energy level of about 18.3 mJ/mm³ for the pulse duration of about 7 ns at FWHM. These results suggested that the skin lesions may be cleared by having more than one treatment at this pulse duration level; for example, by having a second treatment one week after the first. For such treatments, a pulse duration of about 7 ns at FWHM may be used.

As shown in Table 3, when the electrical energy applied per tumor volume was in the range of about 20.3 mJ/mm³ to about 48.9 mJ/mm³, the tumors shrunk at least 15% for 80% of the cases. At this energy level, the tumor growth was prevented in Example 18 by applying electrical pulses with duration of about 7 nanoseconds at FWHM.

The examples summarized Table 3 demonstrated that the skin lesion treatment may be more effective at the pulse duration of about 14 ns at FWHM than at the pulse duration of about 7 ns at FWHM. However, as explained above, at least the tumor growth can be prevented with the pulse duration of about 7 ns at FWHM and more than one treatment is possible.

TABLE 3

Electrical pulses applied to skin lesions and treatment results.

| Example | Pulse Duration at FWHM (ns) | Peak Amplitude of Electrical Pulses (kV) | Number of Electrical Pulses per Application | Electrical Energy Applied per Tumor Volume (mJ/mm$^3$) | Tumor Growth or Shrinkage (%) | Notes |
|---|---|---|---|---|---|---|
| 15 | 7 | 7.00 | 100 | 29.3 | 500 | Tumor grew |
| 16 | 7 | 7.00 | 100 | 24.4 | −89 | Tumor shrunk |
| 18 | 7 | 7.00 | 200 | 48.9 | 0 | Tumor volume not changed |
| 19 | 7 | 7.00 | 200 | 24.4 | −33 | Tumor shrunk |
| 25 | 14 | 5.50 | 200 | 45.1 | −100 | Tumor cleared |
| 27 | 14 | 7.00 | 50 | 27.9 | −100 | Tumor cleared |
| 28 | 14 | 7.00 | 50 | 24.4 | −100 | Tumor cleared |
| 29 | 14 | 7.00 | 50 | 35.1 | −15 | Tumor shrunk |
| 30 | 14 | 7.00 | 50 | 29.2 | −100 | Tumor cleared |
| 31 | 14 | 7.00 | 50 | 20.3 | −100 | Tumor cleared |

As shown in Table 4, when the electrical energy applied per tumor volume was above about 51.6 mJ/mm$^3$, the tumors shrunk at least 50% for all the cases, i.e. 34 cases. In this energy level, the tumors were cleared in more than 90% of the cases. For example, the tumor of Example 36, shown in FIG. 5, cleared within one week, i.e. 100% reduction in volume, after it was treated by applying an electrical energy of about 79.8 mJ/mm$^3$. As shown in FIG. 6, only a scab remained after this treatment.

Examples 60 to 77

Application of Nanosecond Electrical Pulses to Warts

In Examples 60 to 74, common warts, which formed on the skins of human subjects, were treated by using the nanopulse generator and the applicator tip manufactured in the same manner disclosed in Example 1. An open label,

TABLE 4

Electrical pulses applied to skin lesions and treatment results.

| Example | Pulse Duration at FWHM (ns) | Amplitude of Electrical Pulses (kV) | Number of Electrical Pulses per Application | Electrical Energy Applied per Tumor Volume (mJ/mm$^3$) | Tumor Growth or Shrinkage (%) | Notes |
|---|---|---|---|---|---|---|
| 20 | 7 | 7.00 | 400 | 73.3 | −85 | Tumor shrunk |
| 21 | 7 | 7.00 | 400 | 73.3 | −100 | Tumor cleared |
| 22 | 14 | 5.50 | 200 | 60.2 | −50 | Tumor shrunk |
| 23 | 14 | 5.50 | 200 | 60.2 | −100 | Tumor cleared |
| 24 | 14 | 5.50 | 200 | 60.2 | −100 | Tumor cleared |
| 25 | 14 | 5.50 | 200 | 72.2 | −100 | Tumor cleared |
| 26 | 14 | 5.50 | 200 | 51.6 | −100 | Tumor cleared |
| 33 | 14 | 7.00 | 200 | 97.5 | −100 | Tumor cleared |
| 34 | 14 | 7.00 | 200 | 117.0 | −100 | Tumor cleared |
| 35 | 14 | 7.00 | 200 | 92.9 | −100 | Tumor cleared |
| 36 | 14 | 7.00 | 200 | 79.8 | −100 | Tumor cleared, but scab remained |
| 37 | 14 | 7.00 | 200 | 146.2 | −100 | Tumor cleared |
| 38 | 14 | 7.00 | 200 | 117.0 | −100 | Tumor cleared |
| 39 | 14 | 7.00 | 200 | 117.0 | −100 | Tumor cleared |
| 40 | 14 | 7.00 | 200 | 97.5 | −100 | Tumor cleared |
| 41 | 14 | 7.00 | 200 | 73.1 | −100 | Tumor cleared |
| 42 | 14 | 7.00 | 200 | 83.6 | −100 | Tumor cleared |
| 43 | 14 | 7.00 | 200 | 108.3 | −100 | Tumor cleared |
| 44 | 14 | 7.00 | 200 | 146.2 | −100 | Tumor cleared |
| 45 | 14 | 7.00 | 200 | 111.4 | −100 | Tumor cleared |
| 46 | 14 | 7.00 | 400 | 195.0 | −100 | Tumor cleared |
| 47 | 14 | 7.00 | 400 | 146.2 | −100 | Tumor cleared |
| 48 | 14 | 7.00 | 400 | 292.5 | −100 | Tumor cleared |
| 49 | 14 | 7.00 | 400 | 390.0 | −100 | Tumor cleared |
| 50 | 14 | 7.00 | 400 | 234.0 | −100 | Tumor cleared |
| 51 | 14 | 7.00 | 400 | 222.8 | −100 | Tumor cleared |
| 52 | 14 | 7.00 | 400 | 167.1 | −100 | Tumor cleared |
| 53 | 14 | 7.00 | 400 | 222.8 | −100 | Tumor cleared |
| 54 | 14 | 7.00 | 400 | 267.4 | −79 | Tumor shrunk |
| 55 | 14 | 7.00 | 400 | 146.2 | −100 | Tumor cleared |
| 56 | 14 | 7.00 | 400 | 222.8 | −100 | Tumor cleared |
| 57 | 14 | 7.00 | 400 | 162.5 | −100 | Tumor cleared, but scab remained |
| 58 | 14 | 7.00 | 400 | 195.0 | −100 | Tumor cleared, but scab remained |
| 59 | 14 | 7.00 | 400 | 195.0 | −100 | Tumor cleared | non-randomized clinical study was carried out at two study sites to achieve these treatments. Licensed dermatologists treated 15 human subjects. The Food and Drug Administration (FDA) regulations, rules and guidances were followed to manufacture the device and carry out these clinical studies.

Following inclusion criteria were applied in these Examples. Subject must be 18 years of age or older at enrollment. Only common warts are included as study lesions. Up to 2 discrete common warts in a single about 5 cm×about 5 cm anatomical area can be included as study lesions, with up to 2 distinct 5 cm×5 cm areas included. The 5 cm×5 cm area must not have more than 2 warts present at the time of screening and warts outside each area must be at least 2 cm away from warts included as study lesions. A single digit (e.g. finger) can represent the 5 cm×5 cm area, and a lesion within the area can be included as a study lesion unless it is on the inside surface of a digit where there are wart lesions present on the surface of an adjacent digit that would be within 1 cm of touching the potential study lesion when the surfaces of the digits are in contact with one another. Subject's lesions must not protrude more than 5 mm from the skin surface. Subject's lesions may have been treated with over-the-counter treatments, but not by any prescription medicine, surgery, or destructive procedure (i.e., cryotherapy). Subjects' wart and the subject must be suitable candidates for usual Standard of Care treatments. Standard of Care for common warts is defined as curettage and electrodessication, cryotherapy, topical therapy or surgery. Subject must be competent to provide informed consent. If the subject is female, and of childbearing potential, subject must be actively practicing a clinically acceptable form of birth control. Subjects' medical evaluation during their screening visit does not indicate any findings of clinical significance relevant to participating in study. Subject has been informed of their options for standard of care for the lesion type outside of the study.

Following exclusion criteria were applied in these Examples. Subjects not meeting all inclusion criteria should be excluded. Subjects who have lesions within the 5 cm×5 cm anatomical area under study that are painful or have been noticeably changing just prior to the time of screening are excluded. Common wart lesions which are recalcitrant and have not responded to previous office therapy are excluded from the study as study lesions. Periungual warts are excluded from the study as study lesions. Lesions on the face are excluded from the study as study lesions. Lesions which are diagnosed as flat warts, filiform warts, plantar warts, and genital warts are excluded from the study as study lesions. Subjects who are using or intend to use any other warts therapy concomitantly during the study period or within 30 days of their screening visit are excluded. Subjects who are not capable of undergoing surgical standard of care treatment for common warts due to mental or physical limitations are excluded. Subjects in whom a minor surgical procedure is contraindicated (e.g. under advice of their own caring physician) are excluded. Subjects who have an implanted artificial heart valve or other prosthesis requiring prophylactic antibiotic coverage for minor surgical procedures are excluded. Subjects who have an implanted cardiac pacer or defibrillator or other similar life sustaining implanted electrical device are excluded. Subjects who have had any cosmetic or therapeutic procedure (e.g. use of liquid nitrogen, surgical excision, curettage, dermabrasion, medium or greater depth chemical peel, laser resurfacing) within 2 cm of targeted area and margins within 30 days of the screening visit are excluded. Subjects who are immunosuppressed either due to an existing medical diagnosis, or are currently using medications that suppress the immune system (e.g. cyclosporine, prednisone, methotrexate, alefacept, infliximab) or have used these medications within 30 days of the screening visit are excluded. Subjects who, if female, know that they are currently pregnant or are lactating and actively breastfeeding are excluded. Under the Investigator's authority to exclude any participant at his/her discretion, participation in this study is not recommended for this subject.

The restrictions, limitations, exceptions and time periods shown in Table 5 were followed by all subjects upon enrolling and for the duration of the study.

TABLE 5

Restrictions, time periods, limitations and exceptions for the wart studies.

| Restrictions | Time Periods, Limitations and Exceptions |
| --- | --- |
| Any cosmetic or therapeutic procedure (e.g. use of liquid nitrogen, surgical excision, curettage, dermabrasion, medium or greater depth chemical peel, laser resurfacing) | Within 2 cm of targeted area and margins during 4 weeks prior to screening visit Within 10 cm of Nanopulse Application area during the study |
| Hair removal procedures, including wax, crèmes, laser etc. | Within 2 cm of Nanopulse Application area within 30 days of screening visit Within 2 cm of the lesion locations during the study |
| 5-Fluorouracil, imiquimod, diclofenac, masoprocol, or photodynamic therapy | Within 10 cm of the Nanopulse application area during the study. |
| Acid-containing therapeutic products (e.g. salicylic acids or fruit acids, such as α and β hydroxy acids and glycolic acids), topical retinoids or light chemical peels | Within 2 cm of lesion location during 30 days prior to screening visit Within 2 cm of Nanopulse Application area during the study |
| Medications that suppress the immune system (e.g. cyclosporine, prednisone, methotrexate, alefacept, infliximab) | Within 30 days prior to screening visit or anytime during the study |
| Excessive or prolonged exposure to ultraviolet light (e.g. sunlight, tanning booths) | Anytime during the study |
| Topical creams, gels, lotions, oils, artificial tanners, or topical steroids | Anytime during study to Nanopulse Application area |
| Any medications or treatments that might influence the intended effects or mask the side effects of Nanopulse Application, such as the application of topical steroids to the Nanopulse Application area | Anytime during study |

The ground and delivery electrodes had the same length for the same applicator tip. The applicator tips with their electrode length varying in the range of 2 mm to 5 mm were used in the treatments. For the application, whole electrode was inserted in the wart. For example, for about 5 mm long electrodes, insertion length of the electrode was about 5 mm for each delivery of the electrical nanopulses. To avoid formation of air pockets between the electrodes, both the tumor and the electrodes were covered with Aquasonic 100 ultrasound transmission gel.

Treatment procedure comprised one or more treatment sessions per wart per subject. Also, each treatment comprised one or more applications per wart. In each application, about 3200 electrical pulses were applied to each wart with a repetition rate (i.e. frequency) of about 100 Hz. The pulse duration was about 18 ns at FWHM and the pulse amplitude was about 7 kV. Then, for $R_L$ of about 100 ohms, the total energy delivered to the tissue per pulse was calculated to be about 5.88 mJ.

The wart size was measured by using a ruler. The highest elevation of the wart as measured from the healthy skin surface (i.e. protrusion) was recorded as the wart height. The longest length of the wart as measured parallel to the healthy skin surface was recorded as the wart diameter. The wart volume, $Wa_V$ was then calculated by using the following equation:

$$Wa_V = 0.625 \times (\pi \times Wa_D^2/4) \times Wa_H \qquad \text{Equation 7}$$

where $Wa_D$ is the wart diameter and $Wa_H$ is the wart height. The percent of wart growth or shrinkage after each treatment, $Wa_C$ is:

$$Wa_C = 100 \times (Wa_{V,after} - Wa_{V,before}) Wa_{V,before} \qquad \text{Equation 8}$$

where $Wa_{V,after}$ is the wart volume measured after the treatment and $Wa_{V,before}$ is the wart volume measured before the treatment.

The pulse duration at FWHM, the pulse amplitude, and the number of pulses per application were set on the pulse generator. Then, the electrodes were vertically inserted into the wart and the electrical pulses were applied.

Surface of the warts, facing the applicator tip, was generally round. Locations for insertion of the delivery electrode were visually decided and evenly distributed on this surface.

The total electrical energy delivered by the applicator tip per treatment, $E_T$ is:

$$E_T = E_P \times N_P \times A_N \qquad \text{Equation 9}$$

where $N_p$ is the number of pulses per application and $A_N$ is number of applications per wart. Electrical energy delivered per volume of wart, $E_V$ is:

$$E_V = E_T \times Wa_H / (N_H \times Wa_{V,before}) \qquad \text{Equation 10}$$

where $N_H$ is the electrode height.

The applicator tips are designed for single patient use and sterilized between each treatment by using a standard steam autoclave.

Results of the clinical trials are summarized in Table 6. In this table, "NA" means not available.

TABLE 6

Treatment of common warts.

| | | Electrode | Screening Visit | | | | |
|---|---|---|---|---|---|---|---|
| Example | Subject ID | Length (mm) | Date | Wart Location | Diam. (mm) | Height (mm) | Volume (mm³) |
| 60 | 01-207 | 5.00 | Dec. 19, 2011 | Right middle finger, posterior | 5.00 | 1.00 | 12.27 |
| 61 | 01-208 | 5.00 | Feb. 21, 2012 | Dorsal near pinky finger below knuckle | 8.00 | 1.00 | 31.42 |
| 62 | 01-209 | 5.00 | Feb. 29, 2012 | Left hand, posterior, near pinky knuckle | 10.00 | 3.00 | 147.26 |
| 63 | 01-210 | 5.00 | Mar. 5, 2012 | Abdomen | 4.00 | 1.00 | 7.85 |
| 64 | 02-205 | 5.00 | Mar. 12, 2012 | Righ hand, anterior knuckle near ring finger | 8.00 | 3.00 | 94.25 |
| 65 | 01-204 | 5.00 | Jan. 16, 2012 | Left leg, anterior, | 5.00 | 1.00 | 12.27 |
| 66 | 01-201 | 4.00 | Oct. 27, 2011 | Left index finger | 5.00 | 1.00 | 12.27 |
| 67 | 01-203 | 4.00 | Nov. 15, 2011 | Left hand, anterior | 2.00 | 1.00 | 1.96 |
| 68 | 01-201 | 4.00 | Oct. 27, 2011 | Left fourth finger | 6.00 | 1.00 | 17.67 |
| 69 | 01-203 | 4.00 | Nov. 15, 2011 | Left hand, anterior | 3.00 | 1.00 | 4.42 |
| 70 | 01-205 | 5.00 | Jan. 24, 2012 | Right hand, side of pinky finger | 4.00 | 1.00 | 7.85 |
| 71 | 01-206 | 5.00 | Jan. 31, 2012 | Right thumb, medial, anterior | 5.00 | 1.00 | 12.27 |
| 72 | 02-203 | 4.00 | Nov. 28, 2011 | Left posterior hand | 6.00 | 3.00 | 53.01 |
| 73 | 02-203 | 4.00 | Nov. 28, 2011 | Right hand, side of thumb | 3.00 | 1.00 | 4.42 |
| 74 | 02-204 | 4.00 | Dec. 8, 2011 | Left lower leg | 7.00 | 1.00 | 24.05 |
| 75 | 01-202 | 2.00 | Nov. 7, 2011 | Left fourth finger | 2.00 | 2.00 | 3.93 |
| 76 | 02-201 | 5.00 | Oct. 26, 2011 | Right hand | 4.00 | 1.50 | 11.78 |
| 77 | 02-202 | 4.00 | Nov. 8, 2011 | Right posterior arm, | 4.50 | 2.00 | 19.88 |

| | | Treatment 1 | |
|---|---|---|---|
| Example | Date | Number of Applications per Wart (#) | Electrical Energy Applied per Wart Volume (mj/mm³) |
| 60 | Feb. 16, 2012 | 4 | 1227 |
| 61 | Feb. 15, 2012 | 12 | 1437 |

TABLE 6-continued

Treatment of common warts.

| Example | Date | | |
|---|---|---|---|
| 62 | Mar. 1, 2012 | 12 | 920 |
| 63 | Mar. 9, 2012 | 6 | 2875 |
| 64 | Mar. 12, 2012 | 16 | 1917 |
| 65 | Jan. 27, 2012 | 5 | 1533 |
| 66 | Nov. 9, 2011 | 4 | 1533 |
| 67 | Nov. 29, 2011 | 1 | 2396 |
| 68 | Nov. 9, 2011 | 5 | 1331 |
| 69 | Nov. 29, 2011 | 2 | 2130 |
| 70 | Feb. 13, 2012 | 5 | 2396 |
| 71 | Feb. 15, 2012 | 3 | 920 |
| 72 | Nov. 28, 2011 | 10 | 2662 |
| 73 | Nov. 28, 2011 | 8 | 8518 |
| 74 | Dec. 8, 2011 | 11 | 1721 |
| 75 | Nov. 14, 2011 | 4 | 19166 |
| 76 | Oct. 26, 2011 | 11 | 5271 |
| 77 | Nov. 8, 2011 | 10 | 4732 |

| | Evaluation before Treatment 2 | | | | Treatment 2 | | |
| | | | | | | Number of | Electrical Energy |
| Example | Diam. (mm) | Height (mm) | Volume (mm³) | Growth/ Shrink. (%) | Date | Applications per Wart (#) | Applied per Wart Volume (mj/mm³) |
|---|---|---|---|---|---|---|---|
| 60 | NA | NA | NA | NA | | No treatment | |
| 61 | NA | NA | NA | NA | | No treatment | |
| 62 | NA | NA | NA | NA | | No treatment | |
| 63 | NA | NA | NA | NA | | No treatment | |
| 64 | NA | NA | NA | NA | | No treatment | |
| 65 | 0.00 | 0.00 | 0.00 | −100 | Mar. 15, 2012 | No treatment | |
| 66 | 0.00 | 0.00 | 0.00 | −100 | Nov. 22, 2011 | No treatment | |
| 67 | 0.00 | 0.00 | 0.00 | −100 | Dec. 13, 2011 | No treatment | |
| 68 | 5.00 | 0.10 | 1.23 | −93 | Nov. 22, 2011 | 4 | 1533 |
| 69 | 3.00 | 0.10 | 0.44 | −90 | Dec. 13, 2011 | 1 | 1065 |
| 70 | 3.00 | 0.50 | 2.21 | −72 | Mar. 9, 2012 | 4 | 3407 |
| 71 | 2.00 | 0.50 | 0.98 | −92 | Mar. 15, 2012 | 4 | 7666 |
| 72 | 6.00 | 0.10 | 1.77 | −97 | Dec. 14, 2011 | 11 | 2928 |
| 73 | 2.00 | 0.10 | 0.20 | −96 | Dec. 14, 2011 | 6 | 14374 |
| 74 | 6.00 | 1.00 | 17.67 | −27 | Dec. 15, 2011 | 10 | 2130 |
| 75 | 4.00 | 0.10 | 0.79 | −80 | Nov. 28, 2011 | 4 | 4791 |
| 76 | 3.50 | 1.00 | 6.01 | −49 | Nov. 3, 2011 | 11 | 6884 |
| 77 | 4.00 | 2.00 | 15.71 | −21 | Nov. 15, 2011 | 10 | 5989 |

| | Evaluation before Treatment 3 | | | | Treatment 3 | | |
| | | | | | | Number of | Electrical Energy |
| Example | Diam. (mm) | Height (mm) | Volume (mm³) | Growth/ Shrink. (%) | Date | Applications per Wart (#) | Applied per Wart Volume (mj/mm³) |
|---|---|---|---|---|---|---|---|
| 60 | NA | NA | NA | NA | | No treatment | |
| 61 | NA | NA | NA | NA | | No treatment | |
| 62 | NA | NA | NA | NA | | No treatment | |
| 63 | NA | NA | NA | NA | | No treatment | |
| 64 | NA | NA | NA | NA | | No treatment | |
| 65 | NA | NA | NA | NA | | No treatment | |
| 66 | NA | NA | NA | NA | | No treatment | |
| 67 | NA | NA | NA | NA | | No treatment | |
| 68 | NA | NA | NA | NA | | No treatment | |
| 69 | NA | NA | NA | NA | | No treatment | |
| 70 | NA | NA | NA | NA | | No treatment | |
| 71 | NA | NA | NA | NA | | No treatment | |
| 72 | NA | NA | NA | NA | | No treatment | |
| 73 | NA | NA | NA | NA | | No treatment | |
| 74 | NA | NA | NA | NA | | No treatment | |
| 75 | 4.00 | 0.10 | 0.79 | −80 | Dec. 12, 2011 | 4 | 4791 |
| 76 | 3.00 | 1.00 | 4.42 | −63 | Nov. 10, 2011 | 10 | 8518 |
| 77 | 0.00 | 0.00 | 0.00 | −100 | Nov. 29, 2011 | 10 | NA |

| | | Day 45 Evaluation | | | |
| Example | Date | Diam. (mm) | Height (mm) | Volume (mm³) | Growth/Shrink. (%) |
|---|---|---|---|---|---|
| 60 | Mar. 29, 2012 | 4.00 | 0.50 | 3.93 | −68 |
| 61 | Apr. 10, 2012 | 4.00 | 1.00 | 7.85 | −75 |

TABLE 6-continued

Treatment of common warts.

| | | | | | |
|---|---|---|---|---|---|
| 62 | Apr. 17, 2012 | 12.00 | 3.00 | 212.06 | 44 |
| 63 | Apr. 23, 2012 | 5.00 | 0.50 | 6.14 | −22 |
| 64 | Apr. 23, 2012 | 8.00 | 6.00 | 188.50 | 100 |
| 65 | Mar. 21, 2012 | 0.00 | 0.00 | 0.00 | −100 |
| 66 | Dec. 22, 2011 | 0.00 | 0.00 | 0.00 | −100 |
| 67 | Jan. 13, 2012 | 1.50 | 0.10 | 0.11 | −94 |
| 68 | Dec. 22, 2011 | 4.00 | 0.10 | 0.79 | −96 |
| 69 | Jan. 13, 2012 | 2.00 | 0.10 | 0.20 | −96 |
| 70 | Mar. 30, 2012 | 3.00 | 0.50 | 2.21 | −72 |
| 71 | Apr. 4, 2012 | 2.00 | 0.50 | 0.98 | −92 |
| 72 | Jan. 11, 2012 | 3.00 | 0.10 | 0.44 | −99 |
| 73 | Jan. 11, 2012 | 3.00 | 0.10 | 0.44 | −90 |
| 74 | Jan. 25, 2012 | 0.00 | 0.00 | 0.00 | −100 |
| 75 | Jan. 4, 2012 | 5.00 | 1.00 | 12.27 | 213 |
| 76 | Dec. 8, 2011 | 0.00 | 0.00 | 0.00 | −100 |
| 77 | Dec. 22, 2011 | 0.00 | 0.00 | 0.00 | −100 |

Day 90 Evaluation

| Ex. | Date | Diam. (mm) | Height (mm) | Vol. (mm³) | Growth/ Shrink (%) | Duration after Day 45 Evaluation (days) | Number of Treat. Sessions (#) | Concln. |
|---|---|---|---|---|---|---|---|---|
| 60 | May 21, 2012 | 4.00 | 0.50 | 3.93 | −68 | 53 | 1 | Substantial shrinkage |
| 61 | May 21, 2012 | 5.00 | 1.00 | 12.27 | −61 | 41 | 1 | Substantial shrinkage |
| 62 | Jun. 11, 2012 | 12.00 | 2.00 | 141.37 | −4 | 55 | 1 | No change |
| 63 | Jun. 6, 2012 | 5.00 | 1.00 | 12.27 | 56 | 44 | 1 | Growth |
| 64 | Jun. 11, 2012 | 10.00 | 4.00 | 196.35 | 108 | 49 | 1 | Substantial growth |
| 65 | May 4, 2012 | 0.00 | 0.00 | 0.00 | −100 | 44 | 1 | Cleared |
| 66 | Feb. 3, 2012 | 0.00 | 0.00 | 0.00 | −100 | 43 | 1 | Cleared |
| 67 | Feb. 27, 2012 | 1.50 | 0.10 | 0.11 | −94 | 45 | 1 | Substantial shrinkage |
| 68 | Feb. 3, 2012 | 0.00 | 0.00 | 0.00 | −100 | 43 | 2 | Cleared |
| 69 | Feb. 27, 2012 | 3.00 | 0.50 | 2.21 | −50 | 45 | 2 | Substantial shrinkage |
| 70 | May 4, 2012 | 6.00 | 0.25 | 4.42 | −44 | 35 | 2 | Shrinkage |
| 71 | May 23, 2012 | 0.00 | 0.00 | 0.00 | −100 | 49 | 2 | Cleared |
| 72 | Feb. 22, 2012 | 3.00 | 1.00 | 4.42 | −92 | 42 | 2 | Substantial shrinkage |
| 73 | Feb. 22, 2012 | 2.50 | 1.00 | 3.07 | −31 | 42 | 2 | Shrinkage |
| 74 | Mar. 7, 2012 | 1.00 | 0.10 | 0.05 | −100 | 42 | 2 | Substantial shrinkage |
| 75 | Feb. 13, 2012 | 4.00 | 1.00 | 7.85 | 100 | 40 | 3 | Substantial growth |
| 76 | Jan. 26, 2012 | 0.00 | 0.00 | 0.00 | −100 | 49 | 3 | Cleared |
| 77 | Feb. 6, 2012 | 0.00 | 0.00 | 0.00 | −100 | 46 | 3 | Cleared |

In Examples 60 to 67, the treatment comprised one treatment session ("Treatment 1"). In Examples 68 to 74, two such treatment sessions per wart were carried out. Second treatment session, "Treatment 2" was carried out after a time interval varying in the range of about 7 days to about 48 days after Treatment 1. In Examples 75 to 77, three such treatment sessions were carried out at pre-determined time intervals between each treatment session. "Day 90 Evaluation" was carried out about 81 days to about 102 days after Treatment 1.

When the wart volume shrunk to a negligible size (i.e. about 100% shrinkage), it was concluded that the wart was "cleared". In some treatments, the warts did not shrink, but at the same time, they did not grow; that is the wart growth or shrinkage was less than 10%. In these treatments, the wart growth was prevented and the results were recorded as "no change". In examples where the wart shrinkage was in the range of >10% and <50%, it was concluded that there was "shrinkage". In examples where the wart shrinkage was in the range of >50% and <100%, it was concluded that there was "substantial shrinkage". If the wart growth was in the range of >10% to <100%, it was concluded that there was "growth". And if the wart growth was >100%, it was concluded that there was "substantial growth".

In Examples 68, 69, 72, 73 and 75, the height of the warts, which was measured at the evaluation stage before Treatment 2, was negligibly small, i.e. about 0 mm. The wart height for these examples was recorded as about 0.1 mm. Also, in Example 75, the height of the wart, which was measured at the evaluation stage before Treatment 3, was negligibly small, i.e. about 0 mm. The wart height for this example was recorded as about 0.1 mm. Furthermore, in Examples 67-69, 72 and 73, the height of the warts, which was measured at "Day 45 Evaluation", was negligibly small, i.e. about 0 mm. The wart height for these examples was recorded as about 0.1 mm. Similarly, in Examples 67, 69 and 74, the height of the warts, which was measured at "Day 90 Evaluation", was negligibly small, i.e. about 0 mm. The wart height for these examples was also recorded as about 0.1 mm.

All warts shrunk at least 21% after Treatment 1 in all examples where the wart sizes were measured before Treatment 2. These were Examples 65 to 77, i.e. 13 warts in total. The shrinkage was more than 70% for 10 out of these 13 warts (i.e. substantial shrinkage for at least 77% of the cases). And the warts were cleared for three out of these 13 warts (i.e. clearance for at least 20% of the cases). After a single treatment session, when the application energy was at least 920 mJ/mm$^3$, the shrinkage was at least 21% for all warts treated, at least 40% for 85% of the warts treated, and at least 70% for 77% of the warts treated. These results indicated that the electrical energy applied to the wart in one electrical nanopulse treatment session may prevent growth or induce shrinkage of the common warts. These results further indicated that the electrical energy applied to the wart in one electrical nanopulse treatment session may clear the common warts for at least 20% of the cases.

In Examples 60 to 67, only one treatment session was carried out to treat 8 warts in total. The growth was prevented for 6 out of 8 warts (i.e. for at least 75% of cases). The shrinkage was at least 56% for 5 out of 8 warts (i.e. substantial shrinkage for at least 63% of the cases). And the warts were cleared for two out of 8 warts (i.e. clearance for at least 25% of the cases). After the only one treatment session, when the application energy was at least 920 mJ/mm$^3$, the wart growth was at least prevented for at least 75% of cases. And the wart shrinkage was at least 56% for at least 63% cases. These results indicated that one electrical nanopulse treatment may at least prevent growth for at least 75% of cases or induce shrinkage of the common warts for at least 63% cases. These results further indicated that one electrical nanopulse treatment may clear the common warts for at least 25% of the cases.

In Examples 65 to 67, as observed before Treatment 2, the warts were cleared. Therefore, the second treatment session was not carried out in these examples. It was concluded that these warts were cleared with one treatment session.

In Examples 68 to 74, two treatment sessions were carried out to treat 7 warts in total. Day 90 evaluation indicated that at least 31% shrinkage was induced for all these 7 warts (i.e. for 100% cases); at least 50% shrinkage was induced for at least 5 warts out of 7 warts (i.e. substantial shrinkage for at least 71% of cases); and the warts were cleared for at least 2 warts (i.e. for at least 29% of the cases).

In Examples 75 to 77, three treatment sessions were carried out to treat 3 warts in total. Day 90 evaluation indicated that the warts cleared for 2 warts (i.e. for at least 67% of the cases).

Examples 68 to 77 indicated that more than one treatment session may be used to at least prevent growth, or induce shrinkage or clear common warts.

All wart sizes were also measured at "Day 45 Evaluation". Following were concluded when wart sizes measured at "Day 45 Evaluation" were compared with those measured at "Day 90 Evaluation". For 14 out 18 warts (i.e. 78% of the cases), the nanopulse electric treatment induced at least shrinkage that lasted at least 35 days. For example, in Example 60, the shrinkage was 68% as determined at "Day 45 Evaluation". And 53 days after "Day 45 Evaluation", this shrinkage was still 68% as determined at "Day 90 Evaluation". These results indicated that the nanopulse electric treatment may at least prevent growth of the lesion that may last for a duration of at least 35 days. These results further indicated that the nanopulse electric treatment may induce at least shrinkage, or at least substantial shrinkage, or clearance that may last for a duration of at least 35 days. In Examples 60 to 67, the warts were treated with only one treatment session. For these examples, the treatment induced at least substantial shrinkage for 5 out of 8 warts (i.e. about 63% of the cases) that lasted for a duration of at least 41 days. These results indicated that the nanopulse electric treatment comprising only one session may at least prevent growth of the lesion that may last for a duration of at least 41 days. These results further indicated that the nanopulse electric treatment may induce at least shrinkage, or at least substantial shrinkage or clearance that may last for a duration of at least 41 days.

Examples 78 to 87

Application of Nanosecond Electrical Pulses to Actinic Keratosis

In Examples 78 to 87, actinic keratoses, which formed on the skins of human subjects, were treated by using the nanopulse generator and the applicator tip manufactured in the same manner disclosed in Example 1. An open label, non-randomized clinical study was carried out at two study sites to achieve these treatments. Licensed dermatologists treated 10 human subjects. The Food and Drug Administration regulations, rules and guidances were followed to manufacture the device and carry out these clinical studies.

Following inclusion criteria were applied in these Examples. Subject must be 18 years of age or older at enrollment. Primary (non-recurrent), clinically diagnosed actinic keratosis lesions on the scalp, dorsal portions of the hands and dorsal portions of the arms are included. Up to 2 discrete actinic keratosis lesions in a single about 5 cm×about 5 cm anatomical area are included as study lesions, with up to 2 distinct 5 cm×5 cm areas included (up to 4 lesions total). Each 5 cm×5 cm area must not have more than 2 actinic keratosis lesions present at the time of screening and lesions outside each area must be at least 10 mm away from those included as study lesions. Subject's study lesions must be separate from other visible lesions by at least 10 mm. Subjects' actinic keratosis and the subject must be suitable candidates for usual Standard of Care treatments. Standard of care for Actinic Keratosis is defined as cryotherapy. Subject must be competent to provide informed consent. If the subject is female, and of childbearing potential, subject must be actively practicing a clinically acceptable form of birth control. Subjects' medical evaluation during their screening visit does not indicate any findings of clinical significance relevant to participating in study. Subject has been informed of their options for standard of care for the lesion type outside of the study.

Following exclusion criteria were applied in these Examples. Subjects not meeting all inclusion criteria should be excluded. Subject's lesions which have been treated in the past with any modality shall be excluded from the study. Lesions which are painful or noticeably changing shall be excluded from the study. Lesions which are bleeding, weeping or ulcerated shall be excluded from the study. Marked hyperkeratotic, hypertrophic or confluent lesions shall be excluded from the study. No field therapy (such as photodynamic therapy or topical therapeutics) used in the same anatomical area 6 months prior to or during study period. Subjects who have had any cosmetic or therapeutic procedure (e.g. use of liquid nitrogen, surgical excision, curettage, dermabrasion, medium or greater depth chemical peel, laser resurfacing) within 2 cm of targeted lesion area and margins within 30 days of the screening visit. Subjects who are not capable of undergoing surgical standard of care treatment for actinic keratosis due to mental or physical limitations are excluded. Subjects in whom a minor surgical procedure is contraindicated (e.g. under advice of their own caring physician) are excluded. Subjects who have an implanted artificial heart valve or other prosthesis requiring prophylactic antibiotic coverage for minor surgical procedures are excluded. Subjects who have an implanted cardiac pacer or defibrillator or other similar life sustaining implanted electrical device are excluded. Subjects who are immunosuppressed either due to an existing medical diagnosis, or are currently using medications that suppress the immune system (e.g. cyclosporine, prednisone, methotrexate, alefacept, infliximab or any biologics associated with immune suppression) or have used these medications within 30 days of the screening visit are excluded. Subjects who, if female, know that they are currently pregnant or are lactating and actively breastfeeding are excluded. Under the Investigator's authority to exclude any participant at his/her discretion, participation in this study is not recommended for this subject.

The restrictions, limitations, exceptions and time periods shown in Table 7 were followed by all subjects upon enrolling and for the duration of the study.

FWHM and the pulse amplitude was about 7 kV. Then, for $R_L$ of about 100 ohms, the total energy delivered to the tissue per pulse was calculated to be about 5.88 mJ.

The actinic keratosis size was measured by using a ruler. The elevation of the actinic keratosis as measured from the healthy skin surface (i.e. protrusion or height) was negligible, i.e. about 0 mm for all subjects. These heights were recorded as about 0.1 mm. The longest length of the actinic keratosis as measured parallel to the healthy skin surface was recorded as the actinic keratosis diameter. The actinic keratosis volume, $AK_v$ was then calculated by using the following equation:

$$AK_v = 0.625 \times (\pi \times AK_D^2/4) \times AK_H \quad \text{Equation 11}$$

where $AK_D$ is the actinic keratosis diameter and $AK_H$ is the actinic keratosis height. The percent of actinic keratosis growth or shrinkage after each treatment, $AK_D$ is:

$$AK_C = 100 \times (AK_{v,after} - AK_{v,before})/AK_{v,before} \quad \text{Equation 12}$$

TABLE 7

Restrictions, time periods, limitations and exceptions for the wart studies.

| Restrictions | Time Periods, Limitations and Exceptions |
|---|---|
| Any cosmetic or therapeutic procedure (e.g. use of liquid nitrogen, surgical excision, curettage, dermabrasion, medium or greater depth chemical peel, laser resurfacing) | Within 2 cm of targeted area and margins during 4 weeks prior to screening visit<br>Within 5 cm of Nanopulse study lesion locations during the study (except for liquid nitrogen for those study lesions which will be treated using cryotherapy) |
| Hair removal procedures, including wax, crèmes, laser etc. | Within 2 cm of Nanopulse Application area within 30 days of screening visit<br>Within 2 cm of the lesion locations during the study |
| 5-Fluorouracil, imiquimod, diclofenac, masoprocol, or photodynamic therapy | Within 10 cm of the Nanopulse application area during the study. |
| Acid-containing therapeutic products (e.g. salicylic acids or fruit acids, such as α and β hydroxy acids and glycolic acids), topical retinoids or light chemical peels | Within 2 cm of lesion location during 30 days prior to screening visit<br>Within 2 cm of Nanopulse Application area during the study |
| Medications that suppress the immune system (e.g. cyclosporine, prednisone, methotrexate, alefacept, infliximab, or any biologics associated with immune suppression) | Within 30 days prior to screening visit or anytime during the study |
| Excessive or prolonged exposure to ultraviolet light (e.g. sunlight, tanning booths) | Anytime during the study |
| Topical creams, gels, lotions, oils, artificial tanners, or topical steroids | Anytime during study to Nanopulse Application area |
| Any medications or treatments that might influence the intended effects or mask the side effects of Nanopulse Application, such as the application of topical steroids to the Nanopulse Application area | Anytime during study |

The ground and delivery electrodes had the same length for the same applicator tip. The applicator tips with their electrode lengths varying in the range of 2 mm to 5 mm were used in the treatments. For the application, whole electrode was inserted in the wart. For example, for about 5 mm long electrodes, insertion length of the electrode was about 5 mm for each delivery of the electrical nanopulses. To avoid formation of air pockets between the electrodes, both the tumor and the electrodes were covered with Aquasonic 100 ultrasound transmission gel.

Treatment procedure comprised one treatment session per actinic keratosis per subject. Each treatment session comprised one or more applications per actinic keratosis. In each application, about 3200 electrical pulses were applied to each actinic keratosis with a repetition rate (i.e. frequency) of about 100 Hz. The pulse duration was about 18 ns at where $AK_{v,after}$ is the actinic keratosis volume measured after the treatment and $AK_{v,before}$ is the actinic keratosis volume measured before the treatment.

The pulse duration at FWHM, the pulse amplitude, and the number of pulses per application were set on the pulse generator. Then, the electrodes were vertically inserted into the actinic keratosis and the electrical pulses were applied.

Surface of the actinic keratoses, facing the applicator tip, was generally round. Locations for insertion of the delivery electrode were visually decided and evenly distributed on this surface.

The total electrical energy delivered by the applicator tip per treatment, $E_T$ is:

$$E_T = E_P \times N_P \times A_N \quad \text{Equation 13}$$

where $N_P$ is the number of pulses per application and $A_N$ is number of applications per actinic keratosis. Electrical energy delivered per volume of actinic keratosis, $E_V$ is:

$$E_V = E_T / AK_{v,before} \quad \text{Equation 14}$$

where $N_H$ is the electrode height.

The applicator tips are designed for single patient use and sterilized between each treatment by using a standard steam autoclave.

The clinical trial results are summarized in Table 8. In this table, "NA" means not available.

TABLE 8

Treatment of Actinic Keratosis.

| | | Electrode | | Screening Visit | | | |
|---|---|---|---|---|---|---|---|
| Example | Subject ID | Length (mm) | Date | Actinic keratosis location | Diam. (mm) | Height (mm) | Volume (mm³) |
| 78 | 01-301 | 2.00 | Sep. 26, 2011 | Back of left hand | 5.00 | 0.10 | 1.23 |
| 79 | 01-302 | 2.00 | Sep. 27, 2011 | Back of left hand | 8.00 | 0.10 | 3.14 |
| 80 | 01-303 | 2.00 | Sep. 26, 2011 | Back of right hand | 10.00 | 0.10 | 4.91 |
| 81 | 01-304 | 2.00 | Oct. 19, 2011 | Back of right hand | 10.00 | 0.10 | 4.91 |
| 82 | 01-305 | 2.00 | Oct. 18, 2011 | Left forearm | 6.00 | 0.10 | 1.77 |
| 83 | 01-306 | 2.00 | Oct. 19, 2011 | Back of right hand | 10.00 | 0.10 | 4.91 |
| 84 | 01-307 | 4.00 | Nov. 14, 2011 | Left arm | 10.00 | 0.10 | 4.91 |
| 85 | 01-308 | 2.00 | Nov. 28, 2011 | Right hand | 12.00 | 0.10 | 7.07 |
| 86 | 01-309 | 5.00 | Dec. 9, 2011 | Left forearm | 9.00 | 0.10 | 3.98 |
| 87 | 02-301 | 2.00 | Oct. 20, 2011 | Scalp | 4.00 | 0.10 | 0.79 |

| | | Treatment 1 | |
|---|---|---|---|
| Example | Date | Number of Applications per Actinic Keratosis (#) | Electrical Energy Applied per Actinic Keratosis Volume (mj/mm³) |
| 78 | Sep. 27, 2011 | 7 | 5366 |
| 79 | Sep. 29, 2011 | 10 | 2995 |
| 80 | Sep. 29, 2011 | 8 | 1533 |
| 81 | Oct. 27, 2011 | 20 | 3833 |
| 82 | Nov. 7, 2011 | 8 | 4259 |
| 83 | Nov. 8, 2011 | 5 | 958 |
| 84 | Nov. 28, 2011 | 5 | 479 |
| 85 | Dec. 5, 2011 | 4 | 532 |
| 86 | Dec. 16, 2011 | 5 | 473 |
| 87 | Oct. 20, 2011 | 13 | 15572 |

| | | Day 30 Evaluation | | | |
|---|---|---|---|---|---|
| Example | Date | Diam. (mm) | Height (mm) | Volume (mm³) | Growth/Shrink (%) |
| 78 | Oct. 24, 2011 | 0.00 | 0.00 | 0.00 | −100 |
| 79 | Oct. 25, 2011 | 7.00 | 0.10 | 2.41 | −23 |
| 80 | Oct. 25, 2011 | 3.00 | 0.10 | 0.44 | −91 |
| 81 | Nov. 23, 2011 | 11.00 | 0.10 | 5.94 | 21 |
| 82 | Dec. 7, 2011 | 7.00 | 0.10 | 2.41 | 36 |
| 83 | Dec. 9, 2011 | 7.00 | 0.10 | 2.41 | −51 |
| 84 | Jan. 3, 2012 | 11.00 | 0.10 | 5.94 | 21 |
| 85 | Jan. 6, 2012 | 8.00 | 0.00 | 0.00 | −100 |
| 86 | Jan. 9, 2012 | 12.00 | 0.00 | 0.00 | −100 |
| 87 | Nov. 17, 2011 | NA | NA | NA | NA |

| | | Day 60 Evaluation | | | | |
|---|---|---|---|---|---|---|
| Example | Date | Diam. (mm) | Height (mm) | Volume (mm³) | Growth/Shrink (%) | Duration form Day 30 Evaluation (Days) |
| 78 | Nov. 18, 2011 | 6.00 | 0.10 | 1.77 | 44 | 25 |
| 79 | Nov. 28, 2011 | 7.00 | 0.10 | 2.41 | −23 | 34 |
| 80 | Nov. 22, 2011 | 8.00 | 0.10 | 3.14 | −36 | 28 |
| 81 | Dec. 27, 2011 | 12.00 | 0.10 | 7.07 | 44 | 34 |
| 82 | Jan. 5, 2012 | 5.00 | 0.10 | 1.23 | −31 | 29 |
| 83 | Jan. 6, 2012 | 7.00 | 0.10 | 2.41 | −51 | 28 |
| 84 | Jan. 27, 2012 | 0.00 | 0.00 | 0.00 | −100 | 24 |
| 85 | Feb. 3, 2012 | 4.00 | 0.00 | 0.00 | −100 | 28 |
| 86 | Feb. 13, 2012 | 12.00 | 0.00 | 0.00 | −100 | 35 |
| 87 | Dec. 15, 2011 | 0.00 | 0.00 | 0.00 | −100 | 28 |

TABLE 8-continued

Treatment of Actinic Keratosis.

Day 90 Evaluation

| Ex. | Date | Diam. (mm) | Height (mm) | Volume (mm³) | Growth/ Shrink. (%) | Duration form Day 30 Evaluation (Days) | Concln. |
|---|---|---|---|---|---|---|---|
| 78 | Jan. 6, 2012 | 0.00 | 0.00 | 0.00 | −100 | 74 | Cleared |
| 79 | Jan. 3, 2012 | 0.00 | 0.00 | 0.00 | −100 | 70 | Cleared |
| 80 | Jan. 10, 2012 | 0.00 | 0.00 | 0.00 | −100 | 77 | Cleared |
| 81 | Jan. 24, 2012 | 13.00 | 0.10 | 8.30 | 69 | 62 | Growth |
| 82 | Feb. 2, 2012 | 0.00 | 0.00 | 0.00 | −100 | 57 | Cleared |
| 83 | Feb. 3, 2012 | 7.00 | 0.10 | 2.41 | −51 | 56 | Substantial shrinkage |
| 84 | Feb. 14, 2012 | 0.00 | 0.00 | 0.00 | −100 | 42 | Cleared |
| 85 | Mar. 6, 2012 | 5.00 | 0.10 | 1.23 | −83 | 60 | Substantial shrinkage |
| 86 | Mar. 12, 2012 | 7.00 | 0.10 | 2.41 | −40 | 63 | Shrinkage |
| 87 | Jan. 11, 2012 | 0.00 | 0.00 | 0.00 | −100 | 55 | Cleared |

Actinic keratoses were treated in one session ("Treatment 1").

When an actinic keratosis shrunk to a negligible size (i.e. about 100% shrinkage), it was concluded that the actinic keratosis was "cleared". In examples where the actinic keratosis shrinkage was in the range of >10% and <50%, it was concluded that there was "shrinkage". In examples where the actinic keratosis shrinkage was in the range of >50% and <100%, it was concluded that there was "substantial shrinkage". If the actinic keratosis growth was in the range of >10% to <100%, it was concluded that there was "growth".

In Examples 78 to 87, nine out of 10 actinic keratoses shrunk (i.e. 90% of cases) after the single treatment session, as observed at "Day 90 Evaluation". The actinic keratoses were cleared for 6 out of these 10 actinic keratoses (i.e. clearance for at least 60% of the cases). When the application energy was at least 237 mJ/mm³, the actinic keratosis growth was at least prevented for at least 90% of cases. And when the application energy was at least 473 mJ/mm³, the shrinkage was at least 40% for at least 90% of the actinic keratoses cases treated, at least 51% for at least 80% of the cases treated, and at least 83% for at least 60% of the cases treated. These results indicated that single electrical nanopulse treatment session may prevent growth or induce shrinkage of the actinic keratoses for at least 90% of cases. These results further indicated that single electrical nanopulse treatment may clear the actinic keratoses for at least 60% of cases.

In Example 83, the shrinkage of the lesion was about 51% at "Day 30 Evaluation", about 51% at "Day 60 Evaluation", and about 51% at "Day 90 Evaluation". These results indicated that one treatment session may at least prevent the growth of the lesion, or induce at least shrinkage of the lesion or induce at least substantial shrinkage of the lesion, which may last at least 56 days.

Sun radiation particularly, its ultra-violet component, may induce damage to the skin, resulting in aged skin, wrinkled skin, or other sun damaged conditions including actinic keratoses. Since above results indicated that the nanopulse electrical energy treatment may at least prevent growth of actinic keratoses, this treatment may also be used to treat other skin conditions caused by sun radiation.

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications which are set forth in this specification, including in the claims which follow, are approximate, not exact. They are intended to have a reasonable range which is consistent with the functions to which they relate and with what is customary in the art to which they pertain.

All articles, patents, patent applications, and other publications which have been cited in this disclosure are hereby incorporated herein by reference.

Nothing which has been stated or illustrated is intended or should be interpreted to cause a dedication of any component, step, feature, object, benefit, advantage, or equivalent to the public, regardless of whether it is recited in the claims.

We claim:

1. A method of in vivo treatment of a skin lesion of a human in at least one treatment session, the method comprising:
    selecting, based on a type of the skin lesion, a duration of an electrical pulse at a full-width-half-maximum and an amplitude of the electrical pulse, wherein the duration is selected from a range of 0.01 nanoseconds to 1,000 nanoseconds;
    determining at least one of a volume of the skin lesion or a surface area of the skin lesion;
    selecting, based on at least one of the volume of the skin lesion or the surface area of the skin lesion, a configuration of electrodes of a pulse delivery device, wherein the pulse delivery device is configured to deliver electrical energy to the skin lesion through the electrodes;
    determining, prior to a start of a delivery of the electrical energy and based on the duration and the amplitude of the electrical pulse and on the configuration of the electrodes, a total number of electrical pulses to generate, wherein the duration, the amplitude, and the total number of electrical pulses result in the delivery of at least 10 mJ/mm³ of the electrical energy per volume of the skin lesion in the at least one treatment session;

setting, prior to the start of the delivery of the electrical energy, the duration, amplitude, and the total number on a pulse generator, wherein the pulse generator is connected to the pulse delivery device and configured to generate the electrical energy based on the duration, amplitude, and the total number; and delivering the electrical energy of at least 10 mJ/mm$^3$ to the skin lesion through the electrodes of the pulse delivery device.

2. The method of claim 1, wherein the skin lesion comprises malignancies, precancerous lesions, human papilloma virus (HPV) infected cells, immune-related conditions, seborrheic keratosis, acrocordon, aged skin, wrinkled skin, damaged skin, or combinations thereof.

3. The method of claim 1, wherein the skin lesion comprises basal cell carcinoma, squamous cell carcinoma, actinic keratosis, warts, or combinations thereof.

4. The method of claim 1, wherein the skin lesion comprises common warts, actinic keratosis, or combinations thereof.

5. The method of claim 1, wherein the skin lesion comprises common warts.

6. The method of claim 5, wherein the delivered electrical energy per volume of the skin lesion is at least 920 mJ/mm$^3$ for at least to prevent growth of the warts.

7. The method of claim 6, wherein the at least one treatment induces at least 21% shrinkage of the warts.

8. The method of claim 6, wherein the at least one treatment induces at least 40% shrinkage of the warts.

9. The method of claim 6, wherein the at least one treatment induces at least 70% shrinkage of the warts.

10. The method of claim 6, wherein the at least one treatment clears the warts.

11. The method of claim 6, wherein the at least one treatment at least prevents growth of the warts, wherein the prevention of growth lasts at least 41 days.

12. The method of claim 1, wherein the skin lesion comprises actinic keratosis.

13. The method of claim 12, wherein the delivered electrical energy per volume of the skin lesion is at least 473 mJ/mm$^3$ to at least prevent growth of the actinic keratosis.

14. The method of claim 13, wherein the at least one treatment induces at least 20% shrinkage of the actinic keratosis.

15. The method of claim 13, wherein the at least one treatment induces at least 40% shrinkage of the actinic keratosis.

16. The method of claim 13, wherein the at least one treatment induces at least 70% shrinkage of the actinic keratosis.

17. The method of claim 13, wherein the at least one treatment clears the actinic keratoses.

18. The method of claim 13, wherein the at least one treatment prevents at least growth of the actinic keratoses, wherein the prevention of growth lasts at least 56 days.

19. The method of claim 1, wherein the pulse duration at the full-width-half-maximum is in the range of 1 nanoseconds to 100 nanoseconds.

20. The method of claim 1, wherein the pulse duration at the full-width-half-maximum is in the range of 1 nanoseconds to 30 nanoseconds.

21. The method of claim 1, wherein the electrical field formed by each pulse is at least 1 kV/cm at a peak amplitude of the pulse.

22. The method of claim 1, wherein the electrical field formed by each pulse is at least 10 kV/cm at a peak amplitude of the pulse.

23. The method of claim 1, wherein the electrical field formed by each pulse is in the range of 1 kV/cm to 1,000 kV/cm at a peak amplitude of the pulse.

24. The method of claim 1, wherein the electrical field formed by each pulse is in the range of 10 kV/cm to 100 kV/cm at a peak amplitude of the pulse.

25. The method of claim 1, wherein delivering the electrical energy comprises delivering at least 10 electrical pulses.

26. The method of claim 1, wherein delivering the electrical energy comprises delivering at least 100 electrical pulses.

27. The method of claim 1, wherein delivering the electrical energy comprises delivering at least 1,000 electrical pulses.

28. The method of claim 1, wherein the delivered electrical energy per volume of the skin lesion is at least 100 mJ/mm$^3$.

29. The method of claim 1, wherein the delivered electrical energy per volume of the skin lesion is at least 500 mJ/mm$^3$.

30. The method of claim 1, wherein the delivered electrical energy per volume of the skin lesion is at least 1,000 mJ/mm$^3$.

31. The method of claim 1, wherein the delivered electrical energy per volume of the skin lesion is in the range of 10 mJ/mm$^3$ to 10,000 mJ/mm$^3$.

32. The method of claim 1, wherein the at least one treatment comprises a plurality of treatment sessions.

33. The method of claim 1, wherein the at least one treatment comprises at least two treatment sessions.

34. The method of claim 1, wherein the at least one treatment comprises at least three treatment sessions.

* * * * *